(12) United States Patent
Reinmueller et al.

(10) Patent No.: US 10,772,876 B2
(45) Date of Patent: Sep. 15, 2020

(54) ENHANCERS OF NOTCH SIGNALING AND THE USE THEREOF IN THE TREATMENT OF CANCERS AND MALIGNANCIES MEDICABLE BY UPREGULATION OF NOTCH

(71) Applicant: XENIOPRO GmbH, Kelkheim (DE)

(72) Inventors: Viktoria Reinmueller, Allschwil (CH); Jieping Zhu, Lausanne (CH)

(73) Assignee: Xeniopro GmbH, Kelkheim (Taunus) (DE)

( * ) Notice: Subject to any disclaimer, the term of this patent is extended or adjusted under 35 U.S.C. 154(b) by 0 days.

(21) Appl. No.: 16/085,372

(22) PCT Filed: Mar. 17, 2017

(86) PCT No.: PCT/EP2017/056461
§ 371 (c)(1),
(2) Date: Sep. 14, 2018

(87) PCT Pub. No.: WO2017/158190
PCT Pub. Date: Sep. 21, 2017

(65) Prior Publication Data
US 2019/0083476 A1 Mar. 21, 2019

(30) Foreign Application Priority Data
Mar. 17, 2016 (EP) .................................. 16160988

(51) Int. Cl.
| A61K 31/44 | (2006.01) |
| A61K 31/19 | (2006.01) |
| A61K 31/216 | (2006.01) |
| A61P 17/06 | (2006.01) |
| A61P 21/00 | (2006.01) |
| A61K 31/192 | (2006.01) |
| A61P 35/00 | (2006.01) |
| A61P 37/02 | (2006.01) |

(52) U.S. Cl.
CPC ............ *A61K 31/44* (2013.01); *A61K 31/192* (2013.01); *A61K 31/216* (2013.01); *A61P 17/06* (2018.01); *A61P 21/00* (2018.01); *A61P 35/00* (2018.01); *A61P 37/02* (2018.01)

(58) Field of Classification Search
CPC .... A61K 31/44; A61K 31/192; A61K 31/216; A61P 17/06; A61P 21/00; A61P 35/00; A61P 37/02
See application file for complete search history.

(56) References Cited

U.S. PATENT DOCUMENTS

2004/0180889 A1  9/2004  Suto et al.
2015/0307497 A1  10/2015  Sugimoto et al.

FOREIGN PATENT DOCUMENTS

| JP | WO93/24442 A1 * | 12/1993 |
| WO | 9324442 A1 | 12/1993 |
| WO | 9842328 A1 | 10/1998 |
| WO | 03073999 A2 | 9/2003 |
| WO | 2013059582 A2 | 4/2013 |

OTHER PUBLICATIONS

J Mendeleyev et al: "Structural specificity and tumoricidal action of methyl-3,5-diiodo-4-(4'-methoxyphenoxy) benzoate (DIME)", International Journal of Oncology, Apr. 1, 1997 (Apr. 1, 1997), XP055296606, Abstract.
Ayaha Hachisuga et al: "Flying-seed- like liquid crystals 3: new guideline for the induction of mesomorphism by using bulky groups instead of long alkyl chains", Journal of Materials Chemistry C: Materials for Optical and Electronic Devices, vol. I, No. 34, Jan. 1, 2013 (Jan. 1, 2013), p. 5315.
International Search Report cited in PCT/EP2017/056461 dated May 23, 2017, 3 pgs.
Communication pursuant to Article 94(3) EPC cited in EP Application No. 17 710 758.8 dated May 18, 2020, 8 pages.

* cited by examiner

*Primary Examiner* — Timothy R Rozof
(74) *Attorney, Agent, or Firm* — Rothwell, Figg, Ernst & Manbeck, P.C.

(57) ABSTRACT

The present invention relates to the use for enhancing Notch signaling in an individual, of a compound showing the general formula (I) and/or a pharmaceutically acceptable salt or ester thereof, for the treatment of a disease selected from the group of dermatological disorders including atopic dermatitis, psoriasis, immune related disorders, cancer, squamous cell carcinoma, cutaneous and lung squamous cell carcinoma, head and neck cancer, non-melanoma skin cancer, basal cell carcinoma and actinic keratosis, neuroendocrine tumors, neuroendocrine small cell carcinoma and carcinoid tumors, thyroid carcinomas, muscular disorders muscular dystrophy and impaired regeneration capacity after injury; use in immunotherapy for cancer.

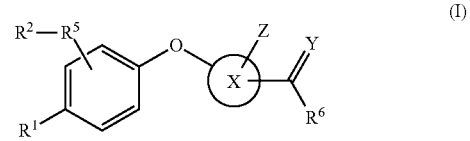

17 Claims, 8 Drawing Sheets

FIG. 2 e)
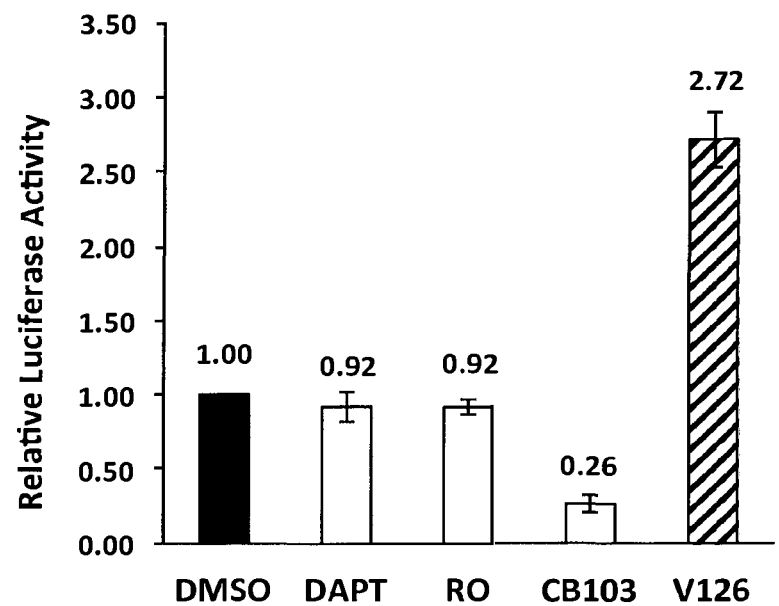
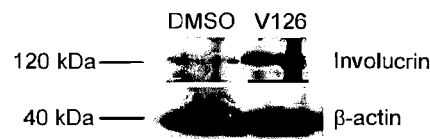
FIG. 3

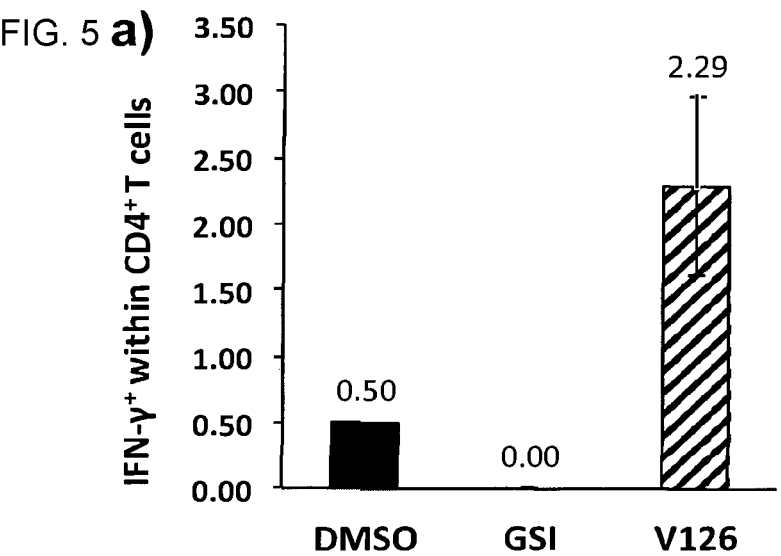
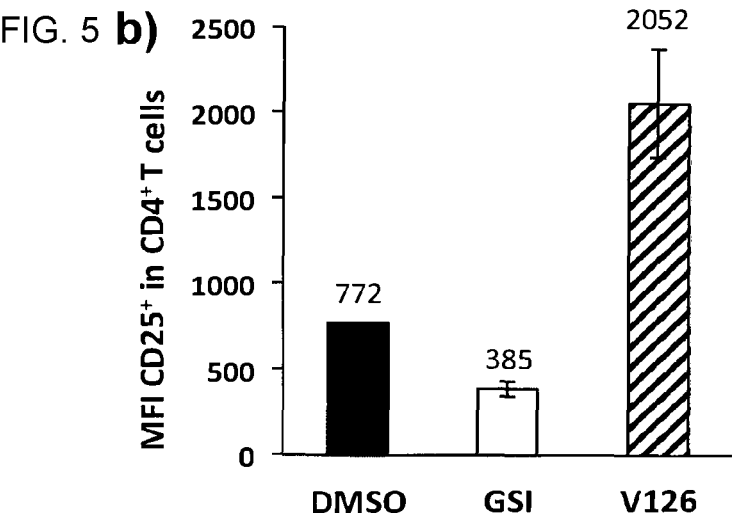

ENHANCERS OF NOTCH SIGNALING AND THE USE THEREOF IN THE TREATMENT OF CANCERS AND MALIGNANCIES MEDICABLE BY UPREGULATION OF NOTCH

CROSS REFERENCE TO RELATED APPLICATION

This application is a 35 U.S.C. 371 National Phase Entry Application from PCT/EP2017/056461, filed Mar. 17, 2017, which claims the benefit of European Patent Application No. 16160988.8 filed on Mar. 17, 2016, the disclosure of which is incorporated herein in its entirety by reference.

FIELD OF THE INVENTION

The present invention relates to compounds which are enhancers of Notch signaling and lend themselves for the treatment of Notch-associated malignancies, such as cancer, degenerative muscle diseases, skin diseases like psoriasis and atopic dermatitis, and immunological disorders, as well as for the use in immunotherapy for cancer.

BACKGROUND OF THE INVENTION

Notch signaling represents a short-range intercellular signaling pathway that plays a critical role during embryogenesis and adult tissue homeostasis. Depending on the cellular context, Notch signaling is involved in the regulation of cell fate determination, differentiation, apoptosis and proliferation, but also in stem cell maintenance. Presence and intensity of Notch signaling in the cellular frame are temporally and spatially strictly controlled. In consequence, abnormal Notch activity can lead to various disease situations. Although Notch was historically identified as an oncogene, studies within the last decade have also demonstrated the tumor suppressive effects of Notch signaling (Koch and Radtke, 2010) (South et al., 2012). In particular in tissues in which Notch signaling induces differentiation such as the skin, and neuroendocrine organs, Notch functions as a tumor suppressor. Thus activating or increasing Notch signaling in cancers including but not limited to cutaneous and lung squamous cell carcinoma (Wang et al., 2011), head and neck cancer (Agrawal et al., 2011; Stransky et al., 2011), neuroendocrine tumors such as thyroid carcinoma (Yu et al., 2013), or neuroendocrine small cell carcinoma (Sriuranpong et al., 2001) and carcinoid tumors (Greenblatt et al., 2007) will induce differentiation and block growth of cancer cells.

Therefore, the development of tools to control Notch signaling is highly desirable. The present invention comprises for use a family of small molecules capable to enhance Notch signaling, resulting in the potential applications, which will be disclosed in the application. The applications are implementable in both human and veterinary medicine.

STATE OF THE ART

WO2013/093885 discloses 6-(4-Tert-Butylphenoxy)Pyridin-3-Amine and derivatives thereof having Notch signalling pathway inhibition properties for the treatment and/or prevention of cancer, wherein the cancer is a Notch dependent cancer, and wherein the Notch dependent cancer is preferably selected from the group comprising T cell-Acute lymphoblastic leukemia (T-ALL), chronic myeloid leukemia (CML), chronic lymphocytic leukemia (CLL), mantle cell lymphoma (MCL), breast cancer, pancreatic cancer, prostate cancer, melanoma, brain tumors, tumor angiogenesis, and colorectal cancer.

Only a limited number of small molecules are reported in the literature that feature to activate Notch signaling, which comprise valproic acid (D. Y. Greenblatt, The Oncologist 2007, 12, 942-951; Mohammed et al., The Oncologist, 2011, 16, 835-843), resveratrol (S. N. Pinchot, Cancer 2011, 117, 7, 1386-1398), phenethyl isothiocyanate (S.-H. Kim, PLoS One 2011, 6, 10) and some flavonoids, such as chrysin (X. M. Yu, Cancer 2013, 119, 4) or hesperetin (P. N. Patel, Ann Surg Oncol 2014). However, some of these molecules showed Notch enhancing properties only at high concentrations. Most of the listed compounds are already in clinical trials being investigated as anticancer drugs for a few different tumor types.

Another approach to upregulate Notch signaling comprises the use of activating Notch ligand-mimicking peptides as for instance a JAG-1 protein peptide fragment (B. J. Nickoloff, Cell Death and Differentiation 2002, 9, 842-855). Nonetheless, this tool to trigger Notch signaling is still in development and only available for research yet. There is a need for potent Notch signaling enhancers that can be used to treat and prevent Notch-associated diseases, preferably dermatologic diseases, immunological disorders, muscular diseases e.g. muscular dystrophy and impaired regeneration capacity after injury, and cancer, e.g. squamous cell carcinoma, neuroendocrine tumors, thyroid carcinomas and others, as well as for immunotherapy against cancer.

The following patent applications and scientific publications may be of interest in the context of the present application:

WO 98/42328, PCT/US98/06037:
"Di-aryl ethers and their derivatives as anti-cancer agents".
WO 93/24442, PCT/JP93/00710:
"Medicine containing benzoic acid derivative as testosterone 5-reductase inhibitor and novel benzoic acid derivative". This application discloses several benzoic acid derivatives which lend themselves as testosterone 5-reductase inhibitors and can, inter alia, be used for the treatment of prostate cancer (prostate carcinoma).
WO 94/05153, PCT/US93/08096:
"Herbicidal benzene compounds".
U.S. Pat. No. 5,438,033, PCT/US92/04644, WO92/22203:
"Substituted pyridine herbicides".

Further patent applications and patents disclosing specific molecular structures are listed in the section Structures tested in the Notch reporter assay.

Chemical and Pharmaceutical Bulletin 1999, 47, 8, 1073-1080, S. Igarashi et al: "A novel class of inhibitors for human steroid 5-reductase: phenoxybenzoic acid derivatives. I".

Bioorganic and Medicinal Chemistry Letters 2011, 21, 4215-4219, C. De Savi et al.: "Selective non zinc binding inhibitors of MMP13".

Bioorganic and Medicinal Chemistry Letters 2012, 22, 1788-1792, T. Nakamura et al.: "Discovery of CS-2100, a potent, orally active and S1P$_3$-sparing S1P$_1$ agonist".

However, all compounds known hitherto which are used as Notch signaling enhancers and treating the diseases related thereto, have the above cited drawbacks Accordingly, one object underlying the present invention is to provide compounds acting as Notch signaling enhancers and which can be used to treat cancers and other diseases which cannot be treated by Notch signaling inhibitors, or provide compounds which render possible an alternative treatment to Notch signaling inhibitors, of the respective diseases. The diseases and cancers are in particular the cancers cited in WO 2013/093885.

A further object underlying the present invention is to provide compounds acting as Notch signaling enhancers, are possible to treat the above-cited diseases and which preferably do not show the drawbacks of the known compounds.

DETAILED DESCRIPTION OF THE INVENTION

The present invention relates to the use for enhancing Notch signaling in an individual, of a compound showing the general formula (I)

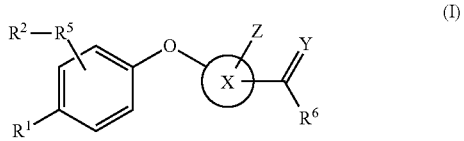

(I)

wherein
X is an aromatic cycle selected from a phenylene ring $C_6H_4$, in which one or more H atoms are optionally replaced independently by one or more of the substituents Z; or X is a 6-membered aromatic heterocycle containing 1 or 2 N atoms, in which one or more H atoms are optionally replaced independently by one or more of the substituents Z;
$R^1$ is selected from: H; linear and branched, unsubstituted and substituted $C_1$-$C_{16}$ alkyl; linear and branched, unsubstituted and substituted $C_2$-$C_8$ alkenyl; linear and branched, unsubstituted and substituted $C_2$-$C_8$ alkynyl; substituted and unsubstituted $C_3$-$C_8$ cycloalkyl; substituted and unsubstituted $C_5$-$C_8$ cycloalkenyl; adamantyl and norbornyl; and wherein the substituents of the named alkyl, alkenyl, alkynyl, cycloalkyl, cycloalkenyl, adamantyl and norbornyl groups are selected from the group F, Cl, Br, I, —CN, —NCO, —NCS, $N_3$, and wherein the named groups can be single or multiple substituted;
$R^2$-$R^5$ are independently of each other selected from: H, F, Cl, Br, I; linear and branched, unsubstituted and substituted $C_1$-$C_4$ alkyl, $C_2$-$C_4$ alkenyl and $C_2$-$C_4$ alkynyl, cyclopropyl and cyclobutyl, and wherein the substituents of the named alkyl, alkenyl, alkynyl, cyclopropyl and cyclobutyl groups are selected from F, Cl, Br and I;
Y is O or S;
Z is selected from: F, Cl, Br, I, linear and branched, unsubstituted and substituted $C_1$-$C_4$ alkyl, $C_2$-$C_4$ alkenyl, $C_2$-$C_4$ alkynyl, cyclopropyl and cyclobutyl, and wherein the substituents of the named alkyl, alkenyl, alkynyl, cyclopropyl and cyclobutyl groups can be selected from F, Cl, Br and I;
$R^6$ is selected from: $OR^7$, $NR^8R^9$, NHOH;
$R^7$ is selected from H and linear and branched $C_1$-$C_6$ alkyl;
$R^8$ and $R^9$ are independently of each other selected from H and linear and branched $C_1$-$C_6$ alkyl;
and/or a pharmaceutically acceptable salt or ester thereof.

The term "substituted" as used herein includes both part and full substitution.

Within the above defined most general embodiment of the invention, the following embodiments A are preferred in case X is a phenylene ring:
$R^1$ is selected from linear and branched, unsubstituted and substituted $C_4$-$C_{16}$ alkyl; linear and branched, substituted and unsubstituted $C_4$-$C_8$ alkenyl; linear and branched, unsubstituted and substituted $C_4$-$C_8$ alkynyl; substituted and unsubstituted $C_4$-$C_8$ cycloalkyl; substituted and unsubstituted $C_5$-$C_8$ cycloalkenyl; adamantyl and norbornyl; and wherein the substituents of the named alkyl, alkenyl, alkynyl, cycloalkyl, cycloalkenyl, adamantyl and norbornyl groups are selected from the group F, Cl, Br, I, —CN, —NCO, —NCS, $N_3$, and wherein the named groups can be single or multiple substituted;
In further embodiments within the above defined most general embodiment, the following embodiments B are preferred in case X is a phenylene ring as depicted in formula Ia:

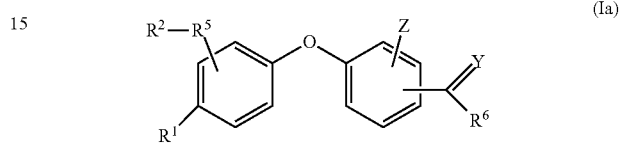

(Ia)

B1: the phenylene ring X is not substituted, or monosubstituted (i.e. contains 0 or 1 substituent Z other than H); and/or
B2: the phenylene ring X is not substituted by I (substituent Z) in position 2 and 6 with respect to the ether group (position o and o'); and/or
B3: the phenylene ring X is not substituted by Br (substituent Z) in position 2 and 6 with respect to the ether group (position o and o'); and/or
B4: the phenylene ring X is not substituted by F, Cl, Br or I (substituent Z) in position 2 and 6 with respect to the ether group (position o and o'); and/or
B5: the phenylene ring X is not substituted by I (substituent Z); and/or
B6: the phenylene ring X is not substituted by F, Cl, Br or I (substituent Z); and/or
B6: the phenylene ring X is not substituted by —$CH_3$ (substituent Z) in position 2 and 6 with respect to the ether group (position o and o'); and/or
B7: the phenylene ring X is not substituted by —$CH_3$, —$C_2H_5$, $C_3H_7$ and/or $C_4H_9$ (substituent Z) in position 2 and 6 with respect to the ether group (position o and o');
B8: the phenylene ring X is not substituted by —$CH_3$, —$C_2H_5$, $C_3H_7$ and/or $C_4H_9$.

The preferred embodiments cited above within the most general embodiment also comprise the combination of embodiment A with each of the embodiments B1, B2, B3, B4, B5, B6, B7 and B8.

It has proved advantageous in case X is a phenylene ring, if $R^1$ is a higher noncyclic or cyclic aliphatic group, starting from $C_4$, i.e. if $R^1$ is a group selected from those which have been cited beforehand within the embodiments A.

The term "alkyl" refers to an aliphatic saturated hydrocarbon group, including methyl ($C_1$ alkyl), ethyl ($C_2$ alkyl), n-propyl, iso-propyl ($C_3$ alkyl), n-butyl, iso-butyl, sec.-butyl and tert.-butyl ($C_4$ alkyl), n-pentyl (amyl), 2-pentyl (sec-pentyl), 3-pentyl; 2-methylbutyl, 3-methylbutyl (iso-pentyl or iso-amyl), 3-methylbut-2-yl, 2-methylbut-2-yl; 2,2-dimethylpropyl (neopentyl) ($C_5$ alkyl), a hexyl group ($C_6$ alkyl) including all isomers, a heptyl group ($C_7$ alkyl) including all isomers, an octyl group ($C_8$ alkyl) including all isomers, a nonyl group including all isomers ($C_9$ alkyl), a decyl group including all isomers ($C_{10}$ alkyl), an undecyl group including all isomers ($C_{11}$ alkyl), a dodecyl group including all isomers ($C_{12}$ alkyl), a tridecyl group including all isomers ($C_{13}$ alkyl), a tetradecyl group group including all isomers ($C_{14}$ alkyl), a pentadecyl group including all isomers ($C_{15}$ alkyl), and a hexadecyl group including all isomers ($C_{16}$ alkyl), as known to the person skilled in the art.

The term "alkenyl" refers to an aliphatic unsaturated hydrocarbon group, including ethenyl ($C_2$ alkenyl), n-propenyl, iso-propenyl ($C_3$ alkenyl), n-butenyl, iso-butenyl, sec.-butenyl and tert.-butenyl ($C_4$ alkenyl), a pentenyl group including all isomers ($C_5$ alkenyl), a hexenyl group ($C_6$ alkenyl) including all isomers, a heptenyl group including all isomers ($C_7$ alkenyl), an octenyl group including all isomers ($C_8$ alkenyl), as known to the person skilled in the art.

The term "alkynyl" refers to the above cited $C_2$-$C_8$ groups having a double bond, but having a triple bond and which are known to the person skilled in the art. Examples include ethynyl ($C_2$ alkynyl), n-propynyl and iso-propynyl ($C_3$ alkynyl), the various isomers of butynyl ($C_4$ alkynyl), the various isomers of pentynyl ($C_5$ alkynyl), the various isomers of hexynyl ($C_6$ alkynyl), the various isomers of heptynyl ($C_7$ alkynyl), and the various isomers of octynyl ($C_8$ alkynyl).

"Cycloalkyl" or "cycloalkyl ring" means an aliphatic cyclic saturated alkyl group, e.g. cyclopropyl ($C_3$ cycloalkyl), cyclobutyl ($C_4$ cycloalkyl), cyclopentyl ($C_5$ cycloalkyl), cyclohexyl ($C_6$ cycloalkyl), cycloheptyl ($C_7$ cycloalkyl), cyclooctyl ($C_8$ cycloalkyl). Each hydrogen of a cycloalkyl carbon may be replaced by a substituent.

"Cycloalkenyl" or "cycloalkenyl ring" means a cyclic unsaturated (one or more double carbon-carbon bonds) aliphatic or aromatic group, e.g. cyclopropenyl ($C_3$ cycloalkenyl), cyclobutenyl ($C_4$ cycloalkenyl), cyclopentenyl ($C_5$ cycloalkenyl), cyclohexenyl ($C_6$ cycloalkenyl), cycloheptenyl ($C_7$ cycloalkenyl), cyclooctenyl ($C_8$ cycloalkenyl). Each hydrogen of a cycloalkyl carbon may be replaced by a substituent.

The substituents $R^2$, $R^3$, $R^4$ and $R^5$ in case these are not H can be in the positions 2, 3, 5 and 6 with respect to the ether group. Preferably, all $R^2$, $R^3$, $R^4$ and $R^5$ are H, or 1 or 2 of $R^2$, $R^3$, $R^4$ and $R^5$ are not H, but selected from the substituents defined above. In the context of the present invention, the term "$R^2$-$R^5$ are independently of each other selected from . . . ." as used throughout the present application means that 1, 2, 3 or 4 of $R^2$, $R^3$, $R^4$ and $R^5$ are other than H, and that each of $R^2$, $R^3$, $R^4$ and $R^5$ can have any of the meanings defined for the respective embodiment.

The carbonyl derived group —C(Y)$R^6$ connected to the aromatic ring can be in position 2, 3 or 4 with respect to the ether bridge, preferably in position 4. This also applies with respect to formula (Ia), which in a preferred embodiment is a phenoxybenzoic acid derivative where the group —C(Y)$R^6$ is in position 4 with respect to the ether bridge (p-position).

The substituent Z can be in the positions 2, 3, 4, 5 and 6 with respect to the ether group.

The term "6-membered aromatic heterocycle containing 1 or 2 N atoms" refers to a heterocycle containing either 1 N atom or 2 N atoms. This heterocycle is selected from pyridine, pyridazine, pyrimidine and pyrazine. In the compounds according to formula (I), the aromatic heterocycle is connected to O in the ether bridge via a chemical bond, and to the carbonyl derived group in another position of the heterocycle, meaning that at least two H atoms in the aromatic heterocycle are replaced by a chemical bond. Further H atoms, for example 1, 2, 3 or 4, preferably 1H atom, may be replaced by the group Z.

In an embodiment of the invention, the Notch signaling enhancing compound belongs to the family of phenoxybenzoic acids and phenoxynicotinic acids and derivatives thereof. The person skilled in the art is aware of appropriate derivates. Known examples include esters and amides.

In a further embodiment of the invention, the invention relates to the compounds as defined in connection with formula (I) and/or a pharmaceutically acceptable salt or ester thereof, including all preferred, more preferred, even more preferred, first most preferred and second most preferred embodiments for the treatment of a disease associated with reduced Notch signaling activity.

In a preferred embodiment of the present invention, the symbols $R^1$ to $R^9$, X, Y and Z have the following meanings: X is an aromatic cycle selected from a phenylene ring $C_6H_4$, in which one or more H atoms are optionally replaced independently by one or more of the substituents Z; or X is a 6-membered aromatic heterocycle containing 1 or 2 N atoms, in which one or more H atoms are optionally replaced independently by one or more of the substituents Z;

$R^1$ is selected from: H; linear and branched, unsubstituted and substituted $C_1$-$C_{12}$ alkyl; linear and branched, unsubstituted and substituted $C_2$-$C_8$ alkenyl; linear and branched, unsubstituted and substituted $C_2$-$C_8$ alkynyl; substituted and unsubstituted $C_3$-$C_8$ cycloalkyl; substituted and unsubstituted $C_5$-$C_8$ cycloalkenyl; adamantyl and norbornyl; and wherein the substituents of the named alkyl, alkenyl, alkynyl, cycloalkyl, cycloalkenyl, adamantyl and norbornyl groups are selected from the group F, Cl, Br, I, —CN, —NCO, —NCS, $N_3$, and wherein the named groups can be single or multiple substituted (i.e. in case the named groups are substituted, they carry one, two or several of the named substituents); $R^2$-$R^5$ are independently of each other selected from: H, F, Cl, Br, I; unsubstituted and substituted $C_1$-$C_2$ alkyl, $C_2$-alkenyl, $C_2$-alkynyl, and wherein the named alkyl, alkenyl, and alkynyl groups can be substituted by F (i.e. in case the named groups are substituted, the substituent is F).
Y is O or S;
Z is selected from F, Cl, Br, I; unsubstituted and substituted $C_1$-$C_2$ alkyl, $C_2$-alkenyl, $C_2$-alkynyl, and wherein the substituent of the named alkyl, alkenyl and alkynyl groups can be F (i.e. in case the named groups are substituted, the substituent is F);
$R^6$ is selected from: $OR^7$, $NR^8R^9$, NHOH;
$R^7$ is selected from H and linear and branched $C_1$-$C_4$ alkyl; and wherein at least one of $R^1$, $R^2$-$R^5$ and Z is a substituent other than H,
$R^8$ and $R^9$ are independently of each other selected from H and linear and branched $C_1$-$C_4$ alkyl.

Within the above defined preferred embodiment of the invention, the following embodiments A are preferred in case X is a phenylene ring:
$R^1$ is selected from linear and branched, unsubstituted and substituted $C_4$-$C_{12}$ alkyl; linear and branched, substituted and unsubstituted $C_4$-$C_8$ alkenyl; linear and branched, unsubstituted and substituted $C_4$-$C_8$ alkynyl; substituted and unsubstituted $C_4$-$C_8$ cycloalkyl; substituted and unsubstituted $C_5$-$C_8$ cycloalkenyl; adamantyl and norbornyl; and wherein the substituents of the named alkyl, alkenyl, alkynyl, cycloalkyl, cycloalkenyl, adamantyl and norbornyl groups are selected from the group F, Cl, Br, I, —CN, —NCO, —NCS, $N_3$, and wherein the named groups can be single or multiple substituted;

In further embodiments within the above defined preferred embodiment, the following embodiments B are preferred in case X is a phenylene ring:
B1: the phenylene ring X is not substituted, or monosubstituted (i.e. contains 0 or 1 substituent Z other than H); and/or B2: the phenylene ring X is not substituted by I (substituent Z) in position 2 and 6 with respect to the ether group (position o and o'); and/or
B3: the phenylene ring X is not substituted by Br (substituent Z) in position 2 and 6 with respect to the ether group (position o and o'); and/or
B4: the phenylene ring X is not substituted by F, Cl, Br or I (substituent Z) in position 2 and 6 with respect to the ether group (position o and o'); and/or
B5: the phenylene ring X is not substituted by I (substituent Z); and/or
B6: the phenylene ring X is not substituted by F, Cl, Br or I (substituent Z); and/or
B6: the phenylene ring X is not substituted by —$CH_3$ (substituent Z) in position 2 and 6 with respect to the ether group (position o and o'); and/or
B7: the phenylene ring X is not substituted by —$CH_3$, —$C_2H_5$, $C_3H_7$ and/or $C_4H_9$ (substituent Z) in position 2 and 6 with respect to the ether group (position o and o');
B8: the phenylene ring X is not substituted by —$CH_3$, —$C_2H_5$, $C_3H_7$ and/or $C_4H_9$.

The preferred embodiments cited above within the above defined preferred embodiment also comprise the combination of embodiment A with each of the embodiments B1, B2, B3, B4, B5, B6, B7 and B8.

It has proved advantageous in case X is a phenylene ring, if $R^1$ is a higher noncyclic or cyclic aliphatic group, starting from $C_4$, i.e. if $R^1$ is a group selected from those which have been cited beforehand within the embodiments A.

In a more preferred embodiment of the present invention, the symbols $R^1$ to $R^9$, X, Y and Z have the following meanings:
X is an aromatic cycle selected from a phenylene ring $C_6H_4$, in which one or more H atoms are optionally replaced independently by one or more of the substituents Z; or X is a 6-membered aromatic heterocycle containing 1 or 2 N atoms, in which one or more H atoms are optionally replaced independently by one or more of the substituents Z;
$R^1$ is selected from: H; linear and branched, unsubstituted and substituted $C_1$-$C_5$ alkyl; linear and branched, unsubstituted and substituted $C_2$-$C_6$ alkenyl; linear and branched, unsubstituted and substituted $C_2$-$C_6$ alkynyl; substituted and unsubstituted $C_3$-$C_6$ cycloalkyl; substituted and unsubstituted $C_5$-$C_6$ cycloalkenyl; adamantyl and norbornyl; and wherein the substituents of the named alkyl, alkenyl, alkynyl, cycloalkyl, cycloalkenyl, adamantyl and norbornyl groups are selected from the group F, Cl, Br, I, —CN, —NCO, —NCS, $N_3$, and wherein the named groups can be single or multiple substituted (i.e. in case the named groups are substituted, they carry one, two or several of the named substituents);
$R^2$-$R^5$ are independently of each other selected from: H, F, Cl, Br, I; unsubstituted and substituted $C_1$-$C_2$ alkyl, $C_2$-alkenyl, and $C_2$-alkynyl, and wherein the substituents of the named alkyl, alkenyl and alkynyl groups can be F (i.e. in case the named groups are substituted, the substituent is F);
Y is O or S;
Z is selected from F, Cl, Br, I; unsubstituted and substituted $C_1$-$C_2$ alkyl $C_2$-alkenyl, and $C_2$-alkynyl, and wherein the substituents of the named alkyl, alkenyl and alkynyl groups can be F (i.e. in case the named groups are substituted, the substituent is F);
$R^6$ is selected from: $OR^7$, $NR^8R^9$, NHOH;
$R^7$ is selected from H and linear and branched $C_1$-$C_4$ alkyl;
$R^8$ and $R^9$ are independently of each other selected from H and linear and branched $C_1$-$C_4$ alkyl.

Within the above defined more preferred embodiment of the invention, the following embodiments A are preferred in case X is a phenylene ring:
$R^1$ is selected from linear and branched, unsubstituted and substituted $C_4$-$C_5$ alkyl; linear and branched, substituted and unsubstituted $C_4$-$C_6$ alkenyl; linear and branched, unsubstituted and substituted $C_4$-$C_6$ alkynyl; substituted and unsubstituted $C_4$-$C_6$ cycloalkyl; substituted and unsubstituted $C_5$-$C_6$ cycloalkenyl; adamantyl and norbornyl; and wherein the substituents of the named alkyl, alkenyl, alkynyl, cycloalkyl, cycloalkenyl, adamantyl and norbornyl groups are selected from the group F, Cl, Br, I, —CN, —NCO, —NCS, $N_3$, and wherein the named groups can be single or multiple substituted (i.e. in case the named groups are substituted, they carry one, two or several of the named substituents);

In further embodiments within the above defined more preferred embodiment, the following embodiments B are preferred in case X is a phenylene ring:
B1: the phenylene ring X is not substituted, or monosubstituted (i.e. contains 0 or 1 substituent Z other than H); and/or
B2: the phenylene ring X is not substituted by I (substituent Z) in position 2 and 6 with respect to the ether group (position o and o'); and/or
B3: the phenylene ring X is not substituted by Br (substituent Z) in position 2 and 6 with respect to the ether group (position o and o'); and/or
B4: the phenylene ring X is not substituted by F, Cl, Br or I (substituent Z) in position 2 and 6 with respect to the ether group (position o and o'); and/or
B5: the phenylene ring X is not substituted by I (substituent Z); and/or
B6: the phenylene ring X is not substituted by F, Cl, Br or I (substituent Z); and/or
B6: the phenylene ring X is not substituted by —$CH_3$ (substituent Z) in position 2 and 6 with respect to the ether group (position o and o'); and/or
B7: the phenylene ring X is not substituted by —$CH_3$, —$C_2H_5$, $C_3H_7$ and/or $C_4H_9$ (substituent Z) in position 2 and 6 with respect to the ether group (position o and o');
B8: the phenylene ring X is not substituted by —$CH_3$, —$C_2H_5$, $C_3H_7$ and/or $C_4H_9$.

The preferred embodiments cited above within the more preferred embodiment also comprise the combination of embodiment A with each of the embodiments B1, B2, B3, B4, B5, B6, B7 and B8.

It has proved advantageous in case X is a phenylene ring, if $R^1$ is a higher noncyclic or cyclic aliphatic group, starting from $C_4$, i.e. if $R^1$ is a group selected from those which have been cited beforehand within the embodiments A.

In an even more preferred embodiment of the present invention, the symbols $R^1$ to $R^9$, X, Y and Z have the following meanings:
X is an aromatic cycle selected from a phenylene ring $C_6H_4$, in which one or more H atoms are optionally replaced independently by one or more of the substituents Z; or X is a 6-membered aromatic heterocycle containing 1 N atom, in which one or more H atoms are optionally replaced independently by one or more of the substituents Z;
$R^1$ is selected from: H; linear and branched, unsubstituted and substituted $C_1$-$C_6$ alkyl; linear and branched, unsubstituted and substituted $C_2$-$C_6$ alkenyl; linear and branched, unsubstituted and substituted $C_2$-$C_6$ alkynyl; substituted and unsubstituted $C_3$-$C_6$ cycloalkyl; substituted and unsubstituted $C_5$-$C_6$ cycloalkenyl; adamantyl and norbornyl; and wherein the named alkyl, alkenyl, alkynyl, cycloalkyl, cycloalkenyl, adamantyl and norbornyl groups can be substituted by F, (i.e. in case the named groups are substituted, the substituent is F), and wherein the named groups can be single or multiple substituted (i.e. in case the named groups are substituted, they carry one, two or more F);
$R^2$-$R^5$ are independently of each other selected from: H; F, Cl, Br, I; unsubstituted and substituted $C_1$-$C_2$ alkyl, $C_2$-alkenyl and $C_2$-alkynyl, and wherein the substituents of the named alkyl, alkenyl and alkynyl groups can be F (i.e. in case the named groups are substituted, the substituent is F);
Y is O or S;
Z is selected from F, Cl, Br, I; unsubstituted and substituted $C_1$-$C_2$ alkyl, $C_2$-alkenyl and $C_2$-alkynyl, and wherein the substituents of the named alkyl, alkenyl and alkynyl groups can be F (i.e. in case the named groups are substituted, the substituent is F);
$R^6$ is selected from: $OR^7$, $NR^8R^9$, NHOH;
$R^7$ is selected from H and linear and branched $C_1$-$C_4$ alkyl;
$R^8$ and $R^9$ are independently of each other selected from H and linear and branched $C_1$-$C_4$ alkyl.

Within the above even more preferred embodiment of the invention, the following embodiments A are preferred in case X is a phenylene ring:
$R^1$ is selected from linear and branched, unsubstituted and substituted $C_4$, $C_5$ and $C_6$ alkyl; linear and branched, substituted and unsubstituted $C_4$, $C_5$ and $C_6$ alkenyl; linear and branched, unsubstituted and substituted $C_4$, $C_5$ and $C_6$ alkynyl; substituted and unsubstituted $C_4$, $C_5$ and $C_6$ cycloalkyl; substituted and unsubstituted $C_5$ and $C_6$ cycloalkenyl; adamantyl and norbornyl; and wherein the substituents of the named alkyl, alkenyl, alkynyl, cycloalkyl, cycloalkenyl, adamantyl and norbornyl groups are selected from the group F, Cl, Br, I, —CN, —NCO, —NCS, $N_3$, and wherein the named groups can be single or multiple substituted (i.e. in case the named groups are substituted, they carry one, two or several of the named substituents);

In further embodiments within the above defined even more preferred embodiment, the following embodiments B are preferred in case X is a phenylene ring:
B1: the phenylene ring X is not substituted, or monosubstituted (i.e. contains 0 or 1 substituent Z other than H); and/or
B2: the phenylene ring X is not substituted by I (substituent Z) in position 2 and 6 with respect to the ether group (position o and o'); and/or
B3: the phenylene ring X is not substituted by Br (substituent Z) in position 2 and 6 with respect to the ether group (position o and o'); and/or
B4: the phenylene ring X is not substituted by F, Cl, Br or I (substituent Z) in position 2 and 6 with respect to the ether group (position o and o'); and/or
B5: the phenylene ring X is not substituted by I (substituent Z); and/or
B6: the phenylene ring X is not substituted by F, Cl, Br or I (substituent Z); and/or
B6: the phenylene ring X is not substituted by —$CH_3$ (substituent Z) in position 2 and 6 with respect to the ether group (position o and o'); and/or
B7: the phenylene ring X is not substituted by —$CH_3$, —$C_2H_5$, $C_3H_7$ and/or $C_4H_9$ (substituent Z) in position 2 and 6 with respect to the ether group (position o and o');
B8: the phenylene ring X is not substituted by —$CH_3$, —$C_2H_5$, $C_3H_7$ and/or $C_4H_9$.

The preferred embodiments cited above within the even more preferred embodiment also comprise the combination of embodiment A with each of the embodiments B1, B2, B3, B4, B5, B6, B7 and B8.

It has proved advantageous in case X is a phenylene ring, if $R^1$ is a higher noncyclic or cyclic aliphatic group, starting from $C_4$, i.e. if $R^1$ is a group selected from those which have been cited beforehand within the embodiments A.

In the first most preferred embodiment of the present invention, the symbols $R^1$ to $R^9$, X, Y and Z have the following meanings:
X is an aromatic cycle selected from a phenylene ring $C_6H_4$, in which one or more H atoms are optionally replaced independently by one or more of the substituents Z; or X is a 6-membered aromatic heterocycle containing 1 N atom, in which one or more H atoms are optionally replaced independently by one or more of the substituents Z;
$R^1$ is selected from: H; linear and branched, unsubstituted and substituted $C_1$-$C_6$ alkyl; substituted and unsubstituted $C_3$-$C_6$ cycloalkyl; adamantyl and norbornyl; and wherein the substituents of the named alkyl, cycloalkyl, adamantyl and norbornyl groups can be F (i.e. in case the named groups are substituted, the substituent is F), and wherein the named groups can be single or multiple substituted (i.e. in case the named groups are substituted, they carry one, two or several F);
$R^2$-$R^5$ are independently of each other selected from: H; F; unsubstituted and substituted $C_1$-$C_2$ alkyl, and wherein the substituents of the named alkyl groups can be F (i.e. in case the named alkyl groups are substituted, the substituent is F);
Y is O.
Z is selected from F, Cl, Br, I; unsubstituted and substituted $C_1$-$C_2$ alkyl, and wherein the named alkyl groups can be substituted by F (i.e. in case the named alkyl groups are substituted, the substituent is F);
$R^6$ is selected from: $OR^7$, $NR^8R^9$;
$R^7$ is selected from H and linear and branched $C_1$-$C_4$ alkyl;
$R^8$ and $R^9$ are independently of each other selected from H and linear and branched $C_1$-$C_4$ alkyl.

In the second most preferred embodiment, the substituents X, $R^2$-$R^5$, Y, Z, and $R^6$-$R^9$ have the same meaning as defined for the first most preferred embodiment, and
$R^1$ is selected from: linear and branched, unsubstituted and substituted $C_1$-$C_6$ alkyl; substituted and unsubstituted $C_3$-$C_6$ cycloalkyl; adamantyl and norbornyl; and wherein the substituents of the named alkyl, cycloalkyl, adamantyl and norbornyl groups can be F (i.e. in case the named groups are substituted, the substituent is F), and wherein the named groups can be single or multiple substituted (i.e. in case the named groups are substituted, they carry one, two or several F).

Within the above defined first and second most preferred embodiment of the invention, the following embodiments A are preferred in case X is a phenylene ring:
$R^1$ is selected from: H, linear and branched, unsubstituted and substituted $C_4$, $C_5$ and $C_6$ alkyl; substituted and unsubstituted $C_4$, $C_5$ and $C_6$ cycloalkyl; adamantyl and norbornyl; and wherein the substituents of the named alkyl, cycloalkyl, adamantyl and norbornyl groups can be F (i.e. in case the named groups are substituted, the substituent is F), and wherein the named groups can be single or multiple substituted, i.e. the named groups can carry one, two or several F (first preferred embodiment); or $R^1$ is selected from: linear and branched, unsubstituted and substituted $C_4$, $C_5$ and $C_6$ alkyl; substituted and unsubstituted $C_4$, $C_5$ and $C_6$ cycloalkyl; adamantyl and norbornyl; and wherein the substituents of the named alkyl, cycloalkyl, adamantyl and norbornyl groups can be F (i.e. in case the named groups are substituted, the substituent is F), and wherein the named groups can be single or multiple substituted (i.e. the named groups can carry one, two or several F) (second preferred embodiment).

In further embodiments within the above defined first and second most preferred embodiment, the following embodiments B are preferred in case X is a phenylene ring:

In further embodiments within the above defined most general embodiment, the following embodiments B are preferred in case X is a phenylene ring:

B1: the phenylene ring X is not substituted, or monosubstituted (i.e. contains 0 or 1 substituent Z other than H); and/or B2: the phenylene ring X is not substituted by I (substituent Z) in position 2 and 6 with respect to the ether group (position o and o'); and/or B3: the phenylene ring X is not substituted by Br (substituent Z) in position 2 and 6 with respect to the ether group (position o and o'); and/or B4: the phenylene ring X is not substituted by F, Cl, Br or I (substituent Z) in position 2 and 6 with respect to the ether group (position o and o'); and/or B5: the phenylene ring X is not substituted by I (substituent Z); and/or B6: the phenylene ring X is not substituted by F, Cl, Br or I (substituent Z); and/or B6: the phenylene ring X is not substituted by —$CH_3$ (substituent Z) in position 2 and 6 with respect to the ether group (position o and o'); and/or B7: the phenylene ring X is not substituted by —$CH_3$, —$C_2H_5$, $C_3H_7$ and/or $C_4H_9$ (substituent Z) in position 2 and 6 with respect to the ether group (position o and o');

B8: the phenylene ring X is not substituted by —$CH_3$, —$C_2H_5$, $C_3H_7$ and/or $C_4H_9$.

The preferred embodiments cited above within the first and second most preferred embodiment also comprise the combination of embodiment A with each of the embodiments B1, B2, B3, B4, B5, B6, B7 and B8.

It has proved advantageous in case X is a phenylene ring, if $R^1$ is a higher noncyclic or cyclic aliphatic group, starting from $C_4$, i.e. if $R^1$ is a group selected from those which have been cited beforehand within the embodiments A.

In another preferred embodiment of the present invention, $R^1$ is selected from: H; linear and branched, unsubstituted and substituted $C_1$-$C_6$ alkyl, preferably linear and branched, substituted an unsubstituted $C_1$-$C_5$ alkyl; substituted and unsubstituted $C_3$-$C_6$ cycloalkyl; adamantanyl and norbornyl; and wherein the named alkyl, cycloalkyl, adamantanyl and norbornyl groups can be substituted by F (i.e. in case the named groups are substituted, the substituent is F), and wherein the named groups can be single or multiple substituted (i.e. the named groups can carry one, two or several F), and $R^2$-$R^5$, X, Y, Z, $R^6$, $R^7$, and $R^8$ and $R^9$ have the meanings as defined in the general, the preferred, the more preferred, the even more preferred, the first most preferred or the second most preferred embodiments.

Within the above defined preferred embodiment of the invention, the following embodiments A are preferred in case X is a phenylene ring:

$R^1$ is selected from: H, linear and branched, unsubstituted and substituted $C_4$, $C_5$ and $C_6$ alkyl; substituted and unsubstituted $C_4$, $C_5$ and $C_6$ cycloalkyl, preferably $C_5$ and $C_6$ cycloalkyl; adamantyl and norbornyl; and wherein the substituents of the named alkyl, cycloalkyl, adamantyl and norbornyl groups can be F (i.e. in case the named groups are substituted, the substituent is F), and wherein the named groups can be single or multiple substituted (i.e. the named groups can carry one, two or several F); and $R^2$-$R^5$, X, Y, Z, $R^6$, $R^7$, and $R^8$ and $R^9$ have the meanings as defined in the preferred, the more preferred, the even more preferred, the first most preferred or the second most preferred embodiments; wherein the substituents and substitution patterns for the phenylene ring X are as set forth in the embodiments B1, B2, B3, B4, B5, B6 and B7.

The present preferred embodiments cited above also comprise the combination of embodiment A with each of the embodiments B1, B2, B3, B4, B5, B6, B7 and B8.

It has proved advantageous in case X is a phenylene ring, if $R^1$ is a higher noncyclic or cyclic aliphatic group, starting from $C_4$, i.e. if $R^1$ is a group selected from those which have been cited beforehand within the embodiments A.

In another preferred embodiment of the present invention, $R^1$ is selected from: linear and branched, unsubstituted and substituted $C_1$-$C_6$ alkyl, preferably linear and branched, substituted an unsubstituted $C_1$-$C_5$ alkyl; substituted and unsubstituted $C_3$-$C_6$ cycloalkyl; adamantanyl and norbornyl; and wherein the named alkyl, cycloalkyl, adamantanyl and norbornyl groups can be substituted by F (i.e. in case the named groups are substituted, the substituent is F), and wherein the named groups can be single or multiple substituted (i.e. the named groups can carry one, two or several F), and $R^2$-$R^5$, X, Y, Z, $R^6$, $R^7$, and $R^8$ and $R^9$ have the meanings as defined in the general, the preferred, the more preferred, the even more preferred, the first most preferred or the second most preferred embodiments.

Within the above defined preferred embodiment of the invention, the following embodiments A are preferred in case X is a phenylene ring:

$R^1$ is selected from: linear and branched, unsubstituted and substituted $C_4$, $C_5$ and $C_6$ alkyl; substituted and unsubstituted $C_4$, $C_5$ and $C_6$ cycloalkyl, preferably $C_5$ and $C_6$ cycloalkyl; adamantyl and norbornyl; and wherein the substituents of the named alkyl, cycloalkyl, adamantyl and norbornyl groups can be F (i.e. in case the named groups are substituted, the substituent is F), and wherein the named groups can be single or multiple substituted (i.e. the named groups can carry one, two or several F); and $R^2$-$R^5$, X, Y, Z, $R^6$, $R^7$, and $R^8$ and $R^9$ have the meanings as defined in the general, the preferred, the more preferred, the even more preferred, the first most preferred or the second most preferred embodiments; wherein the substituents and substitution patterns for the phenylene ring X are as set forth in the embodiments B1, B2, B3, B4, B5, B6 and B7.

The present preferred embodiments cited above also comprise the combination of embodiment A with each of the embodiments B1, B2, B3, B4, B5, B6, B7 and B8.

It has proved advantageous in case X is a phenylene ring, if $R^1$ is a higher noncyclic or cyclic aliphatic group, starting from $C_4$, i.e. if $R^1$ is a group selected from those which have been cited beforehand within the embodiments A.

In another preferred embodiment of the present invention, $R^1$ is a group selected from —$C(CH_3)_3$, —$C(CH_3)_2C_2H_5$, cyclohexyl and adamantanyl, and $R^2$-$R^5$, X, Y, Z, $R^6$, $R^7$, and $R^8$ and $R^9$ have the meanings as defined in the general, the preferred, the more preferred, the even more preferred, the first most preferred or the second most preferred embodiment, including the definitions for the case that X is a substituted or non substituted phenylene group.

In another preferred embodiment of the present invention, the carbonyl derived group —$C(Y)R^6$ connected to the aromatic ring is in position 4 with respect to the ether bridge, and $R^1$, $R^2$-$R^5$, X, Y, Z, $R^6$, $R^7$, and $R^8$ and $R^9$ have the meanings as defined in the general, the preferred, the more preferred, the even more preferred, the first most preferred or the second most preferred embodiment, including the definitions for the case that X is a substituted or non substituted phenylene group.

In another preferred embodiment of the present invention, X is an aromatic cycle selected from a phenylene ring $C_6H_4$, in which one or more H atoms are optionally replaced independently by one or more of the substituents Z; or X is a 6-membered aromatic heterocycle containing 1 N atom, in which one or more H atoms are optionally replaced independently by one or more of the substituents Z; and $R^1$, $R^2$-$R^5$, X, Y, Z, $R^6$, $R^7$, and $R^8$ and $R^9$ have the meanings as defined in the general, the preferred, the more preferred, the even more preferred, the first most preferred or the second most preferred embodiment, including the definitions for the case that X is a substituted or non substituted phenylene group.

In another preferred embodiment of the present invention, X is an aromatic cycle selected from a phenylene ring $C_6H_4$, in which one or more H atoms are optionally replaced independently by one or more of the substituents Z; or X is a 6-membered aromatic heterocycle containing 1 N atom in position 2 with respect to the ether bridge, in which one or more H atoms are optionally replaced independently by one or more of the substituents Z; and $R^1$, $R^2$-$R^5$, X, Y, Z, $R^6$, $R^7$, and $R^8$ and $R^9$ have the meanings as defined in the general, the preferred, the more preferred, the even more preferred, the first most preferred or the second most preferred embodiments, including the definitions for the case that X is a substituted or non substituted phenylene group.

In a further preferred embodiment of the present invention, if X is a phenlyene group, at least one of $R^2$-$R^5$ and Z is a substituent other than H, in case $R^1$ is H or $CH_3$. This applies for the general, the preferred, the more preferred, the even more preferred, the first most preferred or the second most preferred embodiments of the invention The term "individual" as used in the context of the present application includes any kind of animals, preferably mammals, and even more preferred humans.

Preferred compounds according to the present invention showing Notch signaling enhancing activities are depicted below. As the case may be, each compound may fall into the group of the general compounds of the invention as defined in connection with the general formula I, or into the group of preferred compounds, more preferred compounds, even more preferred compounds, first most preferred or second most preferred compounds as defined beforehand.

V042

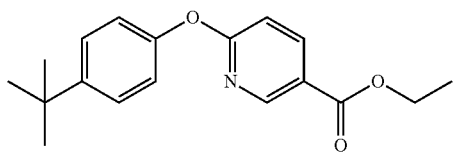

V058

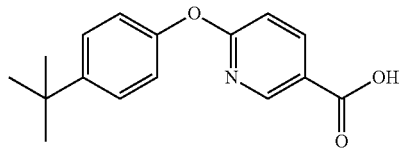

CAS: 1041551-78-3

V111

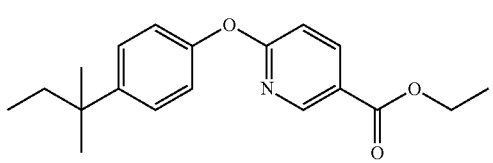

V112

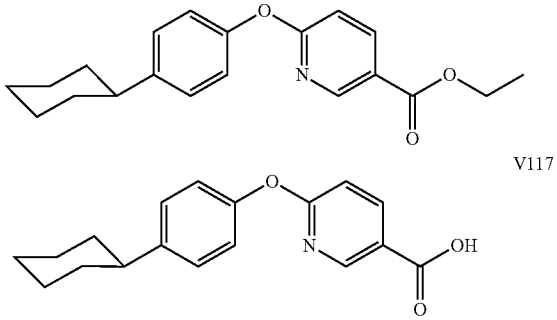

V117

V119

CAS: 1040017-39-7

V122

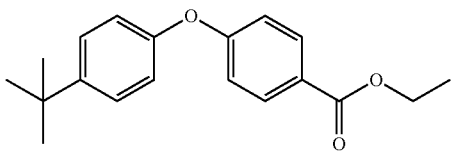

V124

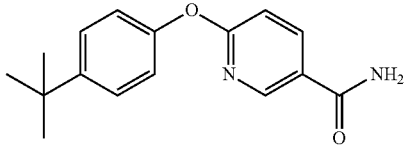

CAS: 900015-10-3

V126

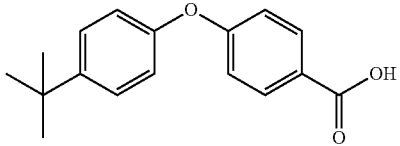

CAS: 925005-92-1

Journal of Materials Chemistry C: Materials for Optical and Electronic Devices (2013), 1 (34), 5315-5321, Hachisuga et al.: "Flying-seed-like liquid crystals 3: new guideline for the induction of mesomorphism by using bulky groups instead of long alkyl chains".

Jpn. Kokai Tokkyo Koho (2012), JP 2012056851 A 20120322, Ito et al.: "Photochemical preparation of aromatic carboxylic acids from aromatic compounds using anthraquinone compounds".

V128

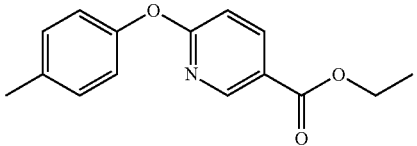

CAS: 1216118-86-3

-continued

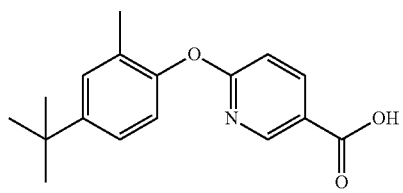
CAS: 1094529-37-9 V134

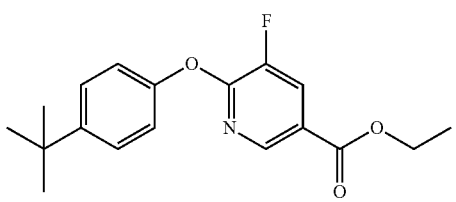
V138

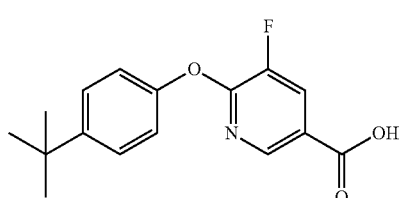
CAS: 1039970-54-1 V142

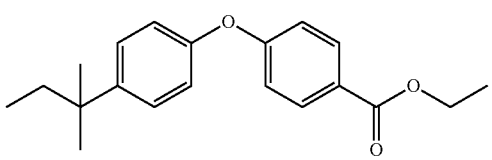
V149

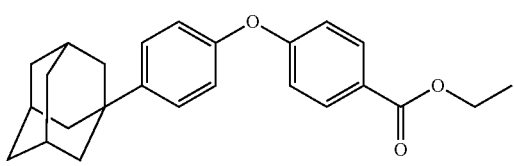
V150

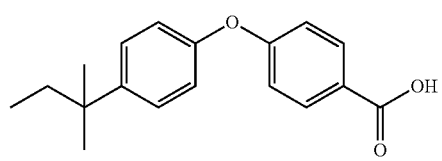
CAS: 938356-51-5 V151

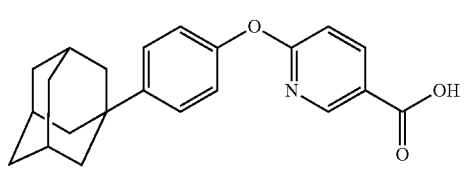
V152

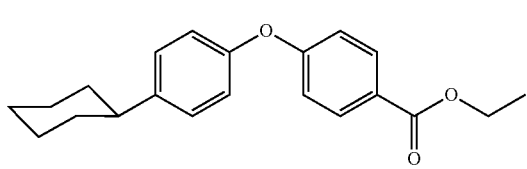
V168

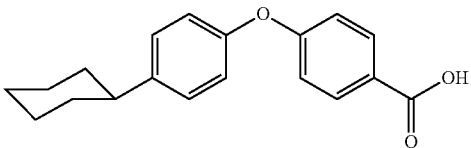
CAS: 158769-86-9 V169

WO 93/24442, PCT/JP93/00710: "Medicine containing benzoic acid derivative as testosterone 5-reductase inhibitor and novel benzoic acid derivative".

The present invention also relates to a compound showing the general formula (I) and/or a pharmaceutically acceptable salt or ester thereof, in all preferred, more preferred, even more preferred, first most preferred and second most preferred embodiments, and of the individual compounds depicted above, for enhancing Notch signaling in an individual.

In a further embodiment of the invention, it relates to the compounds as defined in connection with formula (I) and/or a pharmaceutically acceptable salt or ester thereof, including all preferred, more preferred, even more preferred, first most preferred and second most preferred embodiments, and of the individual compounds depicted above, for the treatment of a disease associated with reduced Notch signaling activity.

The present invention also comprises a method of treating a disease in an individual, comprising administering a compound showing the general formula (I) and/or a pharmaceutically acceptable salt or ester thereof, in all general, preferred, more preferred, even more preferred, first most preferred and second most preferred embodiments, and of the individual compounds depicted above, to the individual.

The diseases which can be treated with the compounds of the invention include diseases selected from the group of dermatological disorders including atopic dermatitis, psoriasis, immune related disorders, cancer including but not limited to squamous cell carcinoma, for example cutaneous and lung squamous cell carcinoma, head and neck cancer, non-melanoma skin cancer, basal cell carcinoma and actinic keratosis, neuroendocrine tumors, for example neuroendocrine small cell carcinoma and carcinoid tumors, thyroid carcinomas; and muscular disorders including muscular dystrophy and impaired regeneration capacity after injury; and the compounds of the invention can be used in immunotherapy for cancer.

In the context of the present application, the term "impaired regeneration after injury" preferably relates to muscle injury caused by: diseases such as muscle dystrophy; exposure to myotoxic agents, such as hypivacaine or lidocaine; sharp or blunt trauma, such as punctures or contusions; ischemia; exposure to hot or cold temperatures; the muscle's own contraction, for example in exercise-induced muscle damage and regeneration, in particular following eccentric exercise.

Diseases which are preferably treated by the compounds of the invention include atopic dermatitis, psoriasis, squamous cell carcinoma, for example cutaneous and lung squamous cell carcinoma, non-melanoma skin cancer, head and neck cancer, basal cell carcinoma and actinic keratosis.

Diseases which are most preferably treated by the compounds of the invention include immune related disorders.

In a further most preferred embodiment of the invention, the compounds are used in immunotherapy for cancer.

Within the teachings of the present invention, the diseases named above in the general, preferred and most preferred embodiments are caused by low Notch signaling and can thus be treated by administering the compounds according to the invention. Preferably, the compounds of the invention are not used for treating prostate cancer (prostate carcinoma), in particular in case X is a phenylene ring.

In a further embodiment of the invention, it relates to the compounds as defined in connection with formula (I)) and/or a pharmaceutically acceptable salt or ester thereof, including all preferred, more preferred, even more preferred, first most preferred and second most preferred embodiments, and of the individual compounds depicted above, for the treatment of a disease selected from the group of dermatological disorders including atopic dermatitis, psoriasis, immune related disorders, cancer including but not limited to squamous cell carcinoma, for example cutaneous and lung squamous cell carcinoma, head and neck cancer, non-melanoma skin cancer, basal cell carcinoma and actinic keratosis; neuroendocrine tumors, for example neuroendocrine small cell carcinoma and carcinoid tumors, and thyroid carcinomas, muscular disorders including muscular dystrophy and impaired regeneration capacity after injury, as well as for the use in immunotherapy for cancer. Preferably, the invention does not relate to the cited compounds for the treatment of prostate cancer (prostate carcinoma), in particular in case X is a phenylene ring.

Diseases which are preferably treated by the compounds of the invention include atopic dermatitis, psoriasis, squamous cell carcinoma, for example cutaneous and lung squamous cell carcinoma, non-melanoma skin cancer, head and neck cancer, basal cell carcinoma and actinic keratosis.

Diseases which are most preferably treated by the compounds of the invention include immune related disorders.

In a further most preferred embodiment of the invention, the compounds are used in immunotherapy for cancer.

The present invention also relates to the compounds as defined in connection with formula (I) and/or a pharmaceutically acceptable salt or ester thereof, including all preferred, more preferred, even more preferred, first most preferred and second most preferred embodiments, and of the individual compounds depicted above, for use as a medicament, except for those compounds of which it is known that they can be used as a medicament (pharmaceutical activity) is known.

Compounds which are described in the art as having a physiological activity are the compounds of formula (Ia) wherein all of $R^2$-$R^5$ are H, the phenylene ring is not substituted by Z, —C(Y)$R^6$ is in position 4 with respect to the ether bridge, Y is O, $R^6$ is O$R^7$, $R^7$ is H, and $R^1$ is H or CH$_3$. These compounds are disclosed in US 2004/0180889, in the context of the treatment of a Pin-1 associated disease including several cancer diseases. No physiological activity for these compounds is shown in the application.

Further compounds according to formula (I) known to have a pharmaceutical activity are the compounds of formula (Ia) wherein all of $R^2$-$R^5$ are H, the phenylene ring is not substituted by Z, —C(Y)$R^6$ is in position 4 with respect to the ether bridge, Y is O, $R^6$ is O$R^7$, $R^7$ is H, and $R^1$ is i-propyl or cyclohexyl; and compounds of formula (Ia) wherein all of $R^2$-$R^5$ are H, the phenylene ring is substituted by Cl (substituent Z) in position 2 with respect to the ether bridge, —C(Y)$R^6$ is in position 4 with respect to the ether bridge, Y is O, $R^6$ is O$R^7$, $R^7$ is H— and $R^1$ is H, i-propyl or norbornyl; and the compound of formula (Ia) wherein all of $R^2$-$R^5$ are H, the phenylene ring is substituted by F (substituent Z) in position 2 with respect to the ether bridge, —C(Y)$R^6$ is in position 4 with respect to the ether bridge, Y is O, $R^6$ is O$R^7$, $R^7$ is H— and $R^1$ is methyl. The above compounds (which include compound V169 as mentioned in the present application) are described in WO 93/24442 as testosterone 5-reductase inhibitors and can, inter alia, be used for the treatment of prostate cancer (prostate carcinoma).

Still, the present invention also relates to the compounds as defined in connection with formula (I), including all preferred, more preferred, even more preferred, first most preferred and second most preferred embodiments as such. Compounds which are known as such are not an embodiment of the present invention. Compounds which are known as such are compounds VO58, V119, V124, V126, V128, V134. V142, V151, and V169.

Still further compounds according to formula (I) known as such are the compounds of formula (Ia) wherein all of $R^2$-$R^5$ are H, the phenylene ring is not substituted by Z, —C(Y)$R^6$ is in position 4 with respect to the ether bridge, Y is O, $R^6$ is O$R^7$, $R^7$ is H— and $R^1$ is i-propyl or cyclohexyl; and compounds of formula (Ia) wherein all of $R^2$-$R^5$ are H, the phenylene ring is substituted by Cl (substituent Z) in position 2 with respect to the ether bridge, —C(Y)$R^6$ is in position 4 with respect to the ether bridge, Y is O, $R^6$ is O$R^7$, $R^7$ is H— and $R^1$ is H, i-propyl or norbornyl; and the compound of formula (Ia) wherein all of $R^2$-$R^5$ are H, the phenylene ring is substituted by F (substituent Z) in position 2 with respect to the ether bridge, —C(Y)$R^6$ is in position 4 with respect to the ether bridge, Y is O, $R^6$ is O$R^7$, $R^7$ is H— and $R^1$ is methyl. The above compounds (which include compound V169 as mentioned in the present application) are described in WO 93/24442.

Further compounds which are described in the art as such are the compounds of formula (Ia) wherein all of $R^2$-$R^5$ are H, the phenylene ring is not substituted by Z, —C(Y)$R^6$ is in position 4 with respect to the ether bridge, Y is O, $R^6$ is O$R^7$, $R^7$ is H— and $R^1$ is H or CH$_3$. These compounds are disclosed in US 2004/0180889.

The present invention also relates to the compounds as defined in connection with formula (I) and/or a pharmaceutically acceptable salt or ester thereof, including all general, preferred, more preferred, even more preferred, first most preferred and second most preferred embodiments, and of the individual compounds depicted above, for use as a medicament in combination therapy, wherein the said compounds are administered in combination with another method of treatment including but not limited to surgery, radiotherapy, chemotherapy, targeted therapy and immunotherapy. The present invention also comprises the use of these above defined compounds in combination therapy for the treatment of for the treatment of a disease selected from the group of dermatological disorders including atopic dermatitis, psoriasis, immune related disorders, cancer including but not limited to squamous cell carcinoma, for example cutaneous and lung squamous cell carcinoma, head and neck cancer, non-melanoma skin cancer, basal cell carcinoma and actinic keratosis; neuroendocrine tumors, for example neuroendocrine small cell carcinoma and carcinoid tumors, and thyroid carcinomas, muscular disorders including muscular dystrophy and impaired regeneration capacity after injury, as well as for the use in immunotherapy for cancer. Preferably, the invention does not relate to the cited compounds for the treatment of prostate cancer (prostate carcinoma), in particular in case X is a phenylene ring.

The term "combination therapy" includes both the sequential and the simultaneous combination of treatments.

The compounds can be used for enhancing Notch signaling, as et forth below.

The Notch receptor is synthesized as a 300 kDa precursor that is cleaved by furin-like convertase(s) in the trans-Golgi compartment. The resulting extracellular/lumenal N-terminal fragment and transmembrane domain/intracellular domain C-terminal fragment are assembled into the mature heterodimer receptor through a noncovalent linkage. The extracellular/lumenal portion of Notch undergoes extensive N- and O-linked glycosylation during Notch synthesis and secretion, which is critical for proper folding of the receptor and its subsequent interactions with ligands. Following export to the cell surface, Notch signal transduction is initiated by ligand binding and endocytosis, which generate the forces needed to expose an otherwise inaccessible ADAM10/TACE/Kuz/SUP-17 cleavage site in the extracellular portion of the Notch C-terminal fragment. Cleavage at this site produces the activated, membrane-anchored Notch form termed Notch extracellular truncation (NEXT). NEXT is subsequently cleaved by the intramembrane aspartyl protease complex γ-secretase, leading to release of the Notch intracellular signal-transducing fragment termed Notch intracellular domain (NICD). This cleavage can occur at the cell surface and within the endosomal trafficking pathway. In the absence of NICD, most Notch target genes are maintained in an actively repressed state through the formation of transcriptional complexes involving CSL transcription factors and various corepressors (CoRep). Upon nuclear translocation of NICD, corepressors associated with CSL are displaced and a transcriptionally active complex consisting of CSL, NICD, Mastermind (Mam), and coactivators (CoAct) assembles, leading to activation of Notch target genes.

This schematic presents a simplified overview of the main conserved features of Notch synthesis and signaling; details of the biochemical mechanisms involved are omitted for the sake of clarity, the positions of the Notch diagrams are not intended to accurately depict the topology of Notch in various membrane compartments, and the glycosylation symbols and transcriptional complex diagrams are illustrative and do not imply specific glycosylation site locations or protein-protein interactions.

Without wishing to be bound by this theory, it is supposed that the compounds of the invention having Notch signaling enhancing properties stabilize the complex CSL-NICD, resulting in an activation of the Notch target genes.

In case of a pathological condition (i.e. in case the individual suffers from a disease as mentioned herein), the administration of a Notch signaling enhancing compound according to the invention leads to either a normalization of the level of the Notch target genes (as found in healthy individuals), or even to a level higher than that found in healthy individuals.

As used herein, the term "enhancing Notch signaling" refers to an effect on a cellular Notch-driven luciferase reporter assay, by which the Notch signaling enhancing properties of the compounds of the invention are determined. The Notch-driven luciferase reporter assay consists of HeLa cells engineered to express the Notch1 full length receptor, and to harbor a CSL-driven firefly luciferase expression construct as well as a Notch independent *Renilla* luciferase construct for the purpose of normalisation. These cells are co-cultured with engineered HeLa cells expressing the Notch ligand Dll4 to induce Notch signaling, thus to induce the expression of the firefly luciferase enzyme. The intensity of a luciferase-driven reporter signal is considered as a measure for Notch signaling.

A compound is considered as having an effect of enhancing Notch signaling if said compound results relative to DMSO in ≥1.5-fold increase, preferably in ≥2.0-fold increase, more preferably in ≥2.5-fold increase and most preferably in ≥3.0-fold increase of the Luciferase-driven reporter signal in the frame of the named Notch-dependent luciferase reporter assay.

Although Notch was historically identified as an oncogene, studies within the last decade have also demonstrated the tumor suppressive effects of Notch signaling (Koch and Radtke, 2010) (South et al., 2012). In particular in tissues in which Notch signaling induces differentiation such as the skin, and neuroendocrine organs, Notch functions as a tumor suppressor. Thus activating or increasing Notch signaling in cancers including but not limited to cutaneous and lung squamous cell carcinoma (Wang et al., 2011), head and neck cancer (Agrawal et al., 2011; Stransky et al., 2011), neuroendocrine tumors such as thyroid carcinoma (Yu et al., 2013), or neuroendocrine small cell carcinoma (Sriuranpong et al., 2001) and carcinoid tumors (Greenblatt et al., 2007) will induce differentiation and block growth of cancer cells.

Some of the compounds of the inventions and/or salts or esters thereof, will exist in different stereoisomeric forms. All of these forms are subjects of the invention. Described below are exemplary salts of the compounds according to the invention which are included herein. The list of the different salts stated below is not meant to be complete and limiting.

Compounds according to the invention which contain one or more acidic groups can be used according to the invention, e.g. as alkali metal salts, alkaline earth metal salts or as ammonium salts. More precise examples of such salts include sodium salts, potassium salts, calcium salts, magnesium salts or salts with ammonia or organic amines such as, e.g. ethylamine, ethanolamine, triethanolamine or amino acids.

Compounds according to the invention which contain one or more basic groups, i.e. groups which can be protonated, can be present and can be used according to the invention in the form of their addition salts with inorganic or organic acids.

Compounds according to the invention which contain a carboxylic acid group or a thiocarboxylic acid group can be used according to the invention in the form of the respective ester. Esters are those according to formula (I) in which H of the carboxy or the thiocarboxy group is replaced by an organic residue. Suitable organic residues are known to a person skilled in the art. Preferred organic residues include the following: An unsubstituted or at least monosubstituted alkyl, preferably a $C_1$-$C_{10}$ alkyl, an alkenyl, preferably $C_2$-$C_{10}$-alkenyl, an alkynyl, preferably $C_3$-$C_{10}$-alkynyl, and an unsubstituted or at least monosubstituted, saturated or unsaturated, non-aromatic or aromatic ring having 3 to 6 C-atoms, and which may contain in the ring one or more heteroatoms from the group N, S or O, and which heteroatom may be identical or different if more than one heteroatom is present. Said substituents being selected from the group consisting of halogen, alkyl, alkenyl, alkynyl, N, S, O, carboxy, sulphonyl, and the like and which can be further substituted.

Examples for current aromatic groups include aryl groups, for example phenyl groups, and heteroaryl groups, which aryl and heteroaryl groups may be substituted, preferably by the substituents given above.

The term "$C_1$-$C_4$-alkyl" refers to methyl, ethyl, n-propyl, iso-propyl, n-butyl, iso-butyl and tert.-butyl.

"$C_{3-7}$ cycloalkyl" or "$C_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Each hydrogen of a cycloalkyl carbon may be replaced by a substituent.

"Heterocyclyl" or "heterocycle" means a cyclopentane, cyclohexane or cycloheptane ring that may contain up to the maximum number of double bonds (aromatic or non-aromatic ring which is fully, partially or un-saturated) wherein at least one carbon atom up to 4 carbon atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a heterocycle include but are not restricted to furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, azepine or homopiperazine. "Heterocycle" means also azetidine.

Examples for suitable salts include hydrogen chloride, hydrogen bromide, phosphoric acid, sulfuric acid, nitric acid, methanesulfonic acid, p-toluenesulfonic acid, napthalenedisulfonic acid, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid and other acids known to a person skilled in the art.

The term "pharmaceutically acceptable" means approved by a regulatory agency such as the EMEA (Europe) and/or the FDA (US) and/or any other national regulatory agency for use in animals, preferably in humans.

Compounds according to the invention which contain several basic groups can simultaneously form different salts.

If a compound according to the invention simultaneously contains acidic and basic groups in the molecule, the invention also includes, in addition to the salt forms mentioned, inner salts or betaines.

The respective salts of the compounds according to the invention can be obtained by customary methods which are known to the person skilled in the art, for example by contacting these with an organic or inorganic acid or base in a solvent or dispersant, or by anion exchange or cation exchange with other salts.

Furthermore, the invention includes all salts of the compounds according to the invention which, owing to low physiological compatibility, are not directly suitable for use in pharmaceuticals but which can be used, for example, as intermediates for chemical reactions or for the preparation of pharmaceutically acceptable salts or which might be suitable for studying Notch signaling activity of a compound according of the invention in any suitable manner, such as any suitable in vitro assay.

The present invention furthermore includes all solvates and tautomers of the compounds according to the invention.

The present invention furthermore includes derivatives/prodrugs (including the salts thereof) of the compounds according to the invention which contain physiologically tolerable and cleavable groups and which are metabolized in animals, preferably mammals, most preferably humans into a compound according to the invention.

The present invention furthermore includes the metabolites of the compounds according to the invention.

The term "metabolites" refers to all molecules derived from any of the compounds according to the invention in a cell or organism, preferably mammal.

Preferably the term relates to molecules which differ from any molecule which is present in any such cell or organism under physiological conditions The structure of the metabolites of the compounds according to the invention will be obvious to any person skilled in the art using the various appropriate methods The compounds according to general formula (I) can be prepared according to methods published in the literature or, respectively, analogous methods.

Methods for the synthesis of the compounds are described e.g., in Houben-Weyl, Methoden der Organischen Chemie (Methods of Organic Chemistry), Thieme-Verlag, Stuttgart, or Organic Reactions, John Wiley & Sons, New York.

Depending on the circumstances of the individual case, in order to avoid side reactions during the synthesis of a compound of the general formula (I), it can be necessary or advantageous to temporarily block functional groups by introducing protective groups and to deprotect them in a later stage of the synthesis, or introduce functional groups in the form of precursor groups which in a later stage are converted into the desired functional groups. Such synthesis strategies and protective groups and precursor groups which are suitable in an individual case are known to the person skilled in the art.

If desired, the compounds of the formula (I) can be purified by customary purification procedures, for example by recrystallization or chromatography. The starting compounds for the preparation of the compounds of the formula (I) are commercially available or can be prepared according to or analogously to literature procedures.

A Detailed Protocol for the Preparation of the Compounds of the Invention is Given Further Below The present invention also relates to a pharmaceutical composition comprising a compound as defined in connection with formula (I), including all preferred, more preferred, even more preferred, first most preferred and second most preferred embodiments, in admixture with an inert carrier, wherein said inert carrier is a pharmaceutical carrier.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

Furthermore, the invention relates to a method for the preparation of a compound according to the invention comprising the steps of coupling, preferably via $S_NAr$ coupling, of substituted phenols with electron-poor aromatic (heteroaromatic) halides. The so-synthesized biaryl ethers are further derivatized by procedures including hydrolysis, esterification and amidation. Compounds can be purified by acid-base extraction, or by column chromatography on silica gel, or precipitation/recrystallization, or by other methods of purification known to a person skilled in the art including preparative thin layer chromatography (TLC) and high performance liquid chromatography (HPLC).

The compounds according to the invention and their pharmaceutically acceptable salts, optionally in combination with other pharmaceutically active compounds suitable to enhance Notch signaling and/or to treat or prevent the above-cited disease or with any other of the drugs known to a person skilled in the art suitable to enhance Notch signaling and/or treat or prevent these diseases can be administered to animals, preferably to mammals, and in particular humans, as pharmaceuticals by themselves, in mixtures with one another or in the form of pharmaceutical preparations.

Various delivery systems are known and can be used to administer a compound of the invention for enhancing Notch signaling and/or to treat the diseases cited, e.g. encapsulation in liposomes, microparticles, and microcapsules:

If not delivered directly to the central nervous system, it is advantageous to select and/or modify methods of administration in such a way as to allow the pharmaceutical compound to cross the blood-brain barrier.

Methods of introduction include, but are not limited to, intradermal, intramuscular, intraperitoneal, intravenous, subcutaneous, intranasal, epidural, and oral routes.

The compounds may be administered by any convenient route, for example by infusion, by bolus injection, by absorption through epithelial or mucocutaneous linings and may be administered together with other biologically active agents.

Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g. by use of an inhaler or nebulizer, and formulation with an aerosolizing agent.

In another embodiment, the therapeutic can be delivered in a vesicle, in particular a liposome (Langer (1990) Science 249:1527-1533; Treat et al. (1989) Liposomes in the Therapy of Infectious Disease and Cancer, Lopez-Berestein and Fidler, eds., Liss, New York, 353-365; Lopez-Berestein, ibid., 317-327)

In yet another embodiment, the therapeutic can be delivered via a controlled release system. In one embodiment, a pump may be used (Sefton (1987) CRC Crit. Ref. Biomed. Eng. 14:201-240; Buchwald et al. (1980) Surgery 88:507-516; Saudek et al. (1989) N. Engl. J. Med. 321:574-579). In another embodiment, polymeric materials can be used (Medical Applications of Controlled Release, Langer and Wise, eds., CRC Press, Boca Raton, Fla. (1974); Controlled Drug Bioavailability, Drug Product Design and Performance, Smolen and Ball, eds., Wiley, New York (1984); Ranger and Peppas (1983) Macromol. Sci. Rev. Macromol. Chem. 23:61; Levy et al. (1985) Science 228:190-192; During et al. (1989) Ann. Neurol. 25:351-356; Howard et al. (1989) J. Neurosurg. 71:858-863). In yet another embodiment, a controlled release system can be placed in proximity of the therapeutic target, i.e., the brain, thus requiring only a fraction of the systemic dose (e.g. Goodson, 1984, In: Medical Applications of Controlled Release, supra, Vol. 2, 115-138). Other controlled release systems are discussed in the review by Langer (1990, Science 249:1527-1533). In order to select an appropriate way of administration, the person skilled in the art will also consider routes of administration which have been selected for other known drugs which enhance Notch signaling or which are used to treat the above-cited diseases. For example, drugs are being taken orally, has been launched both as tablets/liquid and as an i.v.-solution.

In order to select the appropriate dosage, the person skilled in the art will choose a dosage which has been shown to be not toxic in preclinical and/or clinical studies and which can be in accordance with the values given beforehand, or which may deviate from these.

The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 mg/kg body weight to 1 mg/kg body weight. Effective doses may be extrapolated from dose-response curves derived from in vitro or animal model test systems.

Experimental Results

General Procedure A

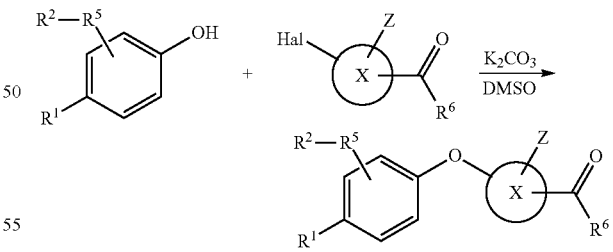

wherein Hal is selected from F and Cl

A solution of the respective phenol and the benzoate derivative or, respectively, the carboxylic acid derivative of an aromatic 6-membered heterocycle having 1 or 2 N-atoms, as defined in connection with formula (I), or their substituted derivatives in an appropriate solvent, preferably a polar aprotic solvent, most preferably DMSO, and preferably under addition of anhydrous $K_2CO_3$, was stirred at a temperature between 80° C. and 120° C. depending on the substrate until the limiting reactant was fully converted. The reaction was quenched by addition of water, extracted with organic solvent (preferably Et₂O, EtOAc and DCM depending on the substrate). The combined organic layers were washed with sat. aqueous NaCl solution, dried over Na₂SO₄ and evaporated to dryness under reduced pressure. The crude product was purified by flash column chromatography to give the desired biarylether.

General Procedure B

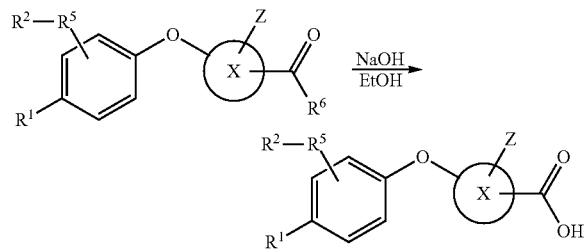

wherein $R^6$ is an alkoxy group, preferably $OC_2H_5$ Hydrolysis of ester: A solution of the respective ester, preferably the ethyl ester in EtOH/0.5 M NaOH was stirred at a temperature between 40° C. and 120° C. depending on the substrate, preferably 80° C. until the complete consumption of the starting materials. The reaction mixture was cooled down to room temperature and then concentrated under reduced pressure. The residue was dissolved in water, acidified, and extracted with an appropriate organic solvent (preferably EtOAC or DCM). The combined organic layers were washed with sat. aqueous NaCl solution, dried over Na₂SO₄ and evaporated to dryness under reduced pressure. The crude product was purified by column chromatography on silica gel, or by recrystallization to give the desired carboxylic acid.

General Procedure C

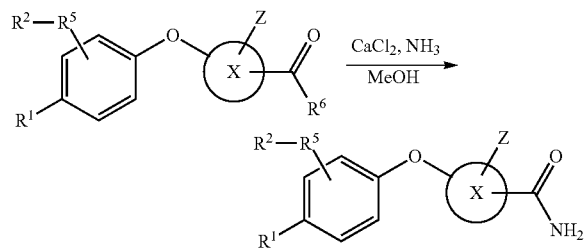

wherein $R^6$ is is an alkoxy group, preferably $OC_2H_5$ Amidation of ester: To a sealed tube were added a solution of the respective ester, preferably the ethyl ester and preferably calcium chloride in an appropriate solvent, preferably MeOH and a solution of NH₃ in an appropriate solvent, preferably MeOH. The mixture was stirred at a temperature between 40° C. and 120° C. depending on the substrate, preferably 80° C. until the reaction was completed. The reaction mixture was cooled down to room temperature and concentrated under reduced pressure. The residue was resolved in EtOAc and sat. aqueous NH₄Cl solution. The aqueous phase was extracted with EtOAc. The combined organic layers were washed with sat. aqueous NaCl solution, dried over Na₂SO₄ and evaporated to dryness under reduced pressure. The crude product was purified by flash column chromatography to give the desired amide.

Ethyl 6-(4-(tert-butyl)phenoxy)nicotinate (VO42)

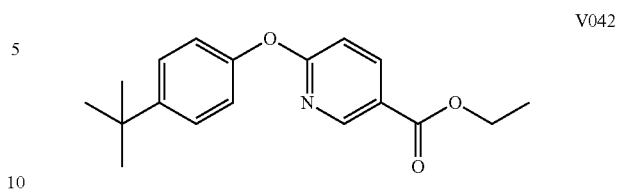

General procedure A: Ethyl 6-chloronicotinate (840 mg, 4.53 mmol, 1.00 equiv), 4-(tert-butyl) phenol (875 mg, 5.82 mmol, 1.29 equiv) and K₂CO₃ (958 mg, 6.93 mmol, 1.53 equiv) in DMSO (5 mL) were stirred at 100° C. for 24 h. Purification by column chromatography (EtOAc/petroleum ether 1/15) gave the desired product as colourless solid (1.23 g, 4.10 mmol, 90%); HRMS (ESI) m/z calcd. for $C_{18}H_{22}NO_3^+$ [M+H]⁺ 300.1594, found: 300.1589; ¹H NMR (400 MHz, Chloroform-d) δ 8.88-8.79 (m, 1H), 8.26 (dd, J=8.6, 2.4 Hz, 1H), 7.46-7.39 (m, 2H), 7.13-7.04 (m, 2H), 6.91 (dd, J=8.6, 0.6 Hz, 1H), 4.37 (q, J=7.1 Hz, 2H), 1.38 (t, J=7.1 Hz, 3H), 1.34 (s, 9H).

6-(4-(tert-Butyl)phenoxy)nicotinic acid (VO58)

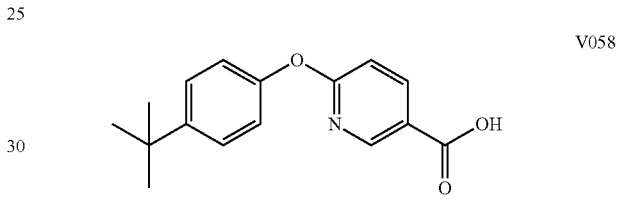

General procedure B: Ethyl 6-(4-(tert-butyl)phenoxy) nicotinate (VO42) (1.22 g, 4.08 mmol, 1.00 equiv) in a mixture of EtOH (12 mL) and 0.5 M NaOH (12 mL) was stirred at 80° C. for 2 h. Filtration of the acidified crude product through cotton using DCM gave the pure desired product without further purification as colourless solid (1.10 g, 4.05 mmol, 99%); HRMS (ESI) m/z calcd. for $C_{16}H_{16}NO_3^-$ [M–H]⁻ 270.1136, found: 270.1134; ¹H NMR (400 MHz, Chloroform-d) δ 11.38 (s, 1H), 8.84 (m, 1H), 8.33-8.30 (m, 1H), 7.45 (d, J=7.9 Hz, 2H), 7.10 (d, J=7.8 Hz, 2H), 6.95 (d, J=8.7 Hz, 1H), 1.35 (s, 9H).

Ethyl 6-(4-(tert-pentyl)phenoxy)nicotinate (V111)

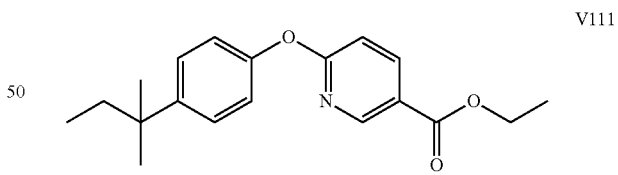

General procedure A: Ethyl 6-chloronicotinate (205 mg, 1.10 mmol, 1.00 equiv), 4-(tert-pentyl) phenol (238 mg, 1.45 mmol, 1.31 equiv) and K₂CO₃ (240 mg, 1.73 mmol, 1.57 equiv) in DMSO (2 mL) were stirred at 80° C. for 4 days. Purification by column chromatography (EtOAc/petroleum ether 1:20) gave the desired product as colourless oil (332 mg, 1.06 mmol, 96%); HRMS (ESI) m/z calcd. for $C_{19}H_{24}NO_3^+$ [M+H]⁺ 314.1751, found: 314.1753; ¹H NMR (400 MHz, Chloroform-d) δ 8.85 (d, J=2.1 Hz, 1H), 8.25 (dd, J=8.6, 2.4 Hz, 1H), 7.36 (d, J=8.7 Hz, 2H), 7.07 (d, J=8.7 Hz, 2H), 6.89 (d, J=8.6 Hz, 1H), 4.36 (q, J=7.1 Hz, 2H), 1.65 (q, J=7.4 Hz, 2H), 1.37 (t, J=7.1 Hz, 3H), 1.29 (s, 6H), 0.71 (t, J=7.4 Hz, 3H).

Ethyl 6-(4-cyclohexylphenoxy)nicotinate (V112)

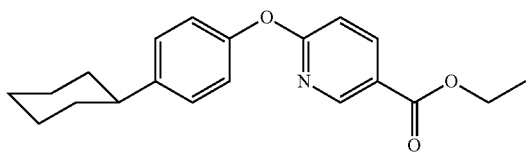

General procedure A: Ethyl 6-chloronicotinate (206 mg, 1.11 mmol, 1.00 equiv), 4-cyclohexylphenol (252 mg, 1.43 mmol, 1.29 equiv) and $K_2CO_3$ (243 mg, 1.76 mmol, 1.58 equiv) in DMSO (2 mL) were stirred at 80° C. for 4 days. Purification by column chromatography (EtOAc/petroleum ether 1/20) gave the desired product as colourless solid (333 mg, 1.02 mmol, 92%); HRMS (ESI) m/z calcd. for $C_{20}H_{24}NO_3^+$ [M+H]$^+$ 326.1751, found: 326.1757; $^1$H NMR (400 MHz, Chloroform-d) δ 8.89 (s, 1H), 8.29 (d, J=8.0 Hz, 1H), 7.28 (d, J=7.6 Hz, 2H), 7.10 (d, J=7.6 Hz, 2H), 6.93 (d, J=8.5 Hz, 1H), 4.41 (q, J=6.7 Hz, 2H), 2.59-2.54 (m, 1H), 1.96-1.88 (m, 4H), 1.81-1.77 (m, 1H), 1.51-1.39 (m, 7H), 1.33-1.23 (m, 1H).

6-(4-Cyclohexylphenoxy)nicotinic acid (V117)

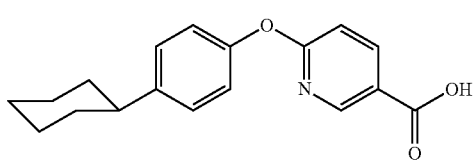

General procedure B: Ethyl 6-(4-cyclohexylphenoxy)nicotinate (V112) (172 mg, 0.53 mmol, 1.00 equiv) in a mixture of EtOH (15 mL) and 0.5 M NaOH (12 mL) was stirred at 80° C. for 6.5 h. Purification of the acidified crude product by recrystallization from DCM gave the desired product as colourless solid (72 mg, 0.24 mmol, 46%); HRMS (ESI) m/z calcd. for $C_{18}H_{20}NO_3^+$ [M+H]$^+$ 298.1438, found: 298.1441; $^1$H NMR (400 MHz, Chloroform-d) δ 8.92 (d, J=2.1 Hz, 1H), 8.31 (dd, J=8.7, 2.3 Hz, 1H), 7.26 (d, J=8.5 Hz, 2H), 7.08 (d, J=8.5 Hz, 2H), 6.94 (d, J=8.7 Hz, 1H), 2.61-2.47 (m, 1H), 1.9-1.85 (m, 4H), 1.77-1.74 (m, 1H), 1.44-1.35 (m, 4H), 1.32-1.20 (m, 1H).

6-(4-(tert-Pentyl)phenoxy)nicotinic acid (V119)

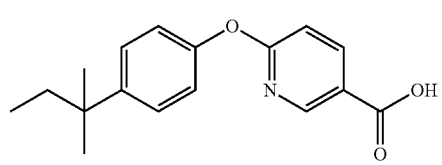

General procedure B: Ethyl 6-(4-(tert-pentyl)phenoxy)nicotinate (V111) (203 mg, 0.65 mmol, 1.00 equiv) in a mixture of EtOH (2 mL) and 0.5 M NaOH (2 mL) was stirred at 80° C. for 30 min. Filtration of the acidified crude product through cotton using EtOAc gave the pure desired product without further purification as colourless solid (185 mg, 0.65 mmol, 100%); HRMS (ESI) m/z calcd. for $C_{17}H_{20}NO_3^+$ [M+H]$^+$ 286.1438, found: 286.1448; $^1$H NMR (400 MHz, Chloroform-d) δ 8.64 (m, 1H), 8.17-8.06 (m, 1H), 7.22 (d, J=8.3 Hz, 2H), 6.91 (d, J=8.3 Hz, 2H), 6.66 (d, J=8.6 Hz, 1H), 1.51 (q, J=7.4 Hz, 2H), 1.15 (s, 6H), 0.57 (t, J=7.4 Hz, 3H).

Ethyl 4-(4-(tert-butyl)phenoxy)benzoate (V122)

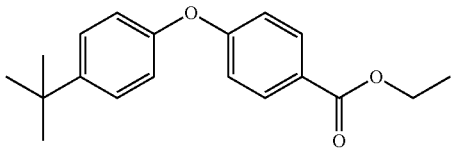

General procedure A: Ethyl 4-fluorobenzoate (808 mg, 4.80 mmol, 1.00 equiv), 4-(tert-butyl) phenol (935 mg, 6.22 mmol, 1.30 equiv) and $K_2CO_3$ (2.22 g, 16.05 mmol, 3.34 equiv) in DMSO (5 mL) were stirred at 100° C. for 10 days. Purification by column chromatography (EtOAc/petroleum ether 1:20) gave the desired product as colourless oil (1.01 g, 3.39 mmol, 71%); HRMS (ESI) m/z calcd. for $C_{19}H_{23}O_3^+$ [M+H]$^+$ 299.1642, found: 299.1648; $^1$H NMR (400 MHz, Chloroform-d) δ 8.00 (d, J=8.8 Hz, 2H), 7.39 (d, J=8.7 Hz, 2H), 6.99 (d, J=8.7 Hz, 2H), 6.98 (d, J=8.9 Hz, 2H), 4.36 (q, J=7.1 Hz, 2H), 1.38 (t, J=7.1 Hz, 3H), 1.34 (s, 9H).

6-(4-(tert-Butyl)phenoxy)nicotinamide (V124)

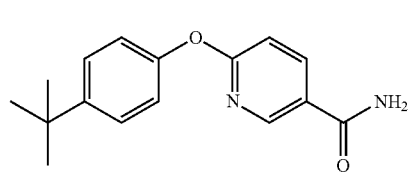

General procedure C: Calcium chloride hexahydrate (82 mg, 0.37 mmol, 1.11 equiv) and ethyl 6-(4-(tert-butyl)phenoxy)nicotinate (VO42) (101 mg, 0.34 mmol, 1.00 equiv) in MeOH (0.5 mL) together with 7 M $NH_3$ in MeOH (0.5 mL, 3.50 mmol, 10 equiv) were stirred at 80° C. for 21 h. Purification by column chromatography on silica gel (DCM/MeOH 4%) gave the desired product as colourless solid (64 mg, 0.24 mmol, 70%); HRMS (ESI) m/z calcd. for $C_{16}H_{19}N_2O_2^+$ [M+H]$^+$ 271.1441, found: 271.1456; $^1$H NMR (400 MHz, Chloroform-d) δ 8.61 (d, J=1.9 Hz, 1H), 8.14 (dd, J=8.6, 2.3 Hz, 1H), 7.42 (d, J=8.6 Hz, 2H), 7.06 (d, J=8.6 Hz, 2H), 6.91 (d, J=8.6 Hz, 1H), 6.32 (s, 2H), 1.33 (s, 9H).

4-(4-(tert-Butyl)phenoxy)benzoic acid (V126)

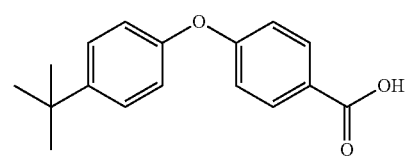

General procedure B: Ethyl 4-(4-(tert-butyl)phenoxy)benzoate (V122) (727 mg, 2.44 mmol, 1.00 equiv) in a mixture of EtOH (7.5 mL) and 0.5 M NaOH (7.5 mL) was stirred at 80° C. for 1 h. Filtration of the acidified crude product through cotton using DCM gave the pure desired product without further purification as colourless solid (614 mg, 2.27 mmol, 93%); HRMS (ESI) m/z calcd. for $C_{17}H_{19}O_3^+$ [M+H]$^+$ 271.1329, found: 271.1330; $^1$H NMR (400 MHz, Chloroform-d) δ 8.07 (d, J=8.8 Hz, 2H), 7.41 (d, J=8.7 Hz, 2H), 7.01 (d, J=8.7 Hz, 2H), 7.01 (d, J=8.8 Hz, 2H), 1.35 (s, 9H).

Ethyl 6-(p-tolyloxy)nicotinate (V128)

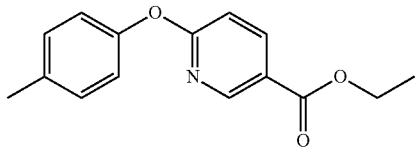

General procedure A: Ethyl 6-chloronicotinate (207 mg, 1.12 mmol, 1.00 equiv), p-cresol (164 mg, 1.52 mmol, 1.36 equiv) and $K_2CO_3$ (235 mg, 1.70 mmol, 1.53 equiv) in DMSO (1.5 mL) were stirred at 80° C. for 4 days. Purification by column chromatography (EtOAc/petroleum ether 1:10) gave the desired product as colourless solid (271 mg, 1.05 mmol, 94%); HRMS (ESI) m/z calcd. for $C_{15}H_{16}NO_3^+$ [M+H]$^+$ 258.1125, found: 258.1131; $^1$H NMR (400 MHz, Chloroform-d) δ 8.82 (m, 1H), 8.25 (dd, J=8.6, 2.4 Hz, 1H), 7.21 (d, J=8.2 Hz, 2H), 7.03 (d, J=8.4 Hz, 2H), 6.90 (d, J=8.6 Hz, 1H), 4.37 (q, J=7.1 Hz, 2H), 2.37 (s, 3H), 1.37 (t, J=7.1 Hz, 3H).

Ethyl 6-(4-(tert-butyl)-2-methylphenoxy)nicotinate (V131)

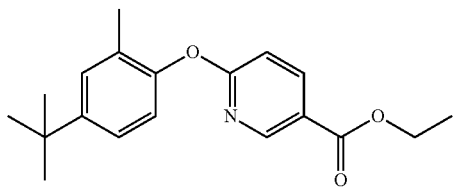

General procedure A: Ethyl 6-chloronicotinate (210 mg, 1.13 mmol, 1.00 eq.), 4-(tert-butyl)-2-methylphenol (245 mg, 1.49 mmol, 1.32 equiv) and $K_2CO_3$ (247 mg, 1.79 mmol, 1.58 equiv) in DMSO (2 mL) were stirred at 80° C. for 3 days. Purification by column chromatography (EtOAc/petroleum ether 1:20) gave the desired product as colourless oil (259 mg, 0.83 mmol, 73%); HRMS (ESI) m/z calcd. for $C_{19}H_{24}NO_3^+$ [M+H]$^+$ 314.1751, found: 314.1759; $^1$H NMR (400 MHz, Chloroform-d) δ 8.92-8.78 (m, 1H), 8.25 (dd, J=8.7, 2.4 Hz, 1H), 7.28 (d, J=2.4 Hz, 1H), 7.27-7.23 (m, 1H), 6.99 (d, J=8.3 Hz, 1H), 6.87 (dd, J=8.7, 0.6 Hz, 1H), 4.37 (q, J=7.1 Hz, 2H), 2.15 (s, 3H), 1.37 (t, J=7.1 Hz, 3H), 1.34 (s, 9H).

6-(4-(tert-Butyl)-2-methylphenoxy)nicotinic acid (V134)

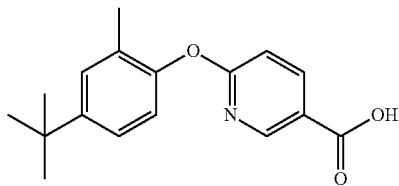

General procedure B: Ethyl 6-(4-(tert-butyl)-2-methylphenoxy)nicotinate (V131) (160 mg, 0.51 mmol, 1.00 equiv) in a mixture of EtOH (4 mL) and 0.5 M NaOH (2 mL) was stirred at 80° C. for 1.5 h. Filtration of the acidified crude product through cotton using DCM gave the pure desired product without further purification as colourless solid (146 mg, 0.51 mmol, 100%); HRMS (ESI) m/z calcd. for $C_{17}H_{20}NO_3^+$ [M+H]$^+$ 286.1438, found: 286.1435; $^1$H NMR (400 MHz, Chloroform-d) δ 9.76 (s, 1H), 8.93 (d, J=2.0 Hz, 1H), 8.31 (dd, J=8.7, 2.4 Hz, 1H), 7.30 (d, J=2.3 Hz, 1H), 7.29-7.25 (m, 1H), 7.01 (d, J=8.3 Hz, 1H), 6.91 (d, J=8.7 Hz, 1H), 2.16 (s, 3H), 1.34 (s, 9H).

Ethyl 4-(4-(tert-butyl)phenoxy)-3-fluorobenzoate (V138)

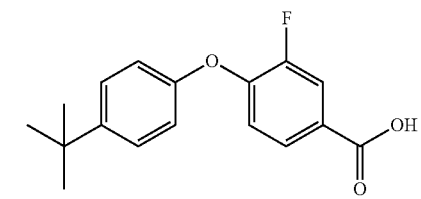

General procedure A: Ethyl 3,4-difluorobenzoate (348 mg, 1.87 mmol, 1.00 equiv), 4-(tert-butyl) phenol (336 mg, 2.24 mmol, 1.20 equiv) and $K_2CO_3$ (388 mg, 2.80 mmol, 1.50 equiv) in DMSO (2 mL) were stirred at 100° C. for 22 h. Purification by column chromatography (EtOAc/petroleum ether 1/40) gave the desired product as colourless oil (451 mg, 1.43 mmol, 76%); HRMS (ESI) m/z calcd. for $C_{19}H_{22}O_3F^+$ [M+H]$^+$ 317.1547, found: 317.1549; $^1$H NMR (400 MHz, Chloroform-d) δ 7.85 (dd, J=11.2, 2.0 Hz, 1H), 7.80-7.73 (m, 1H), 7.42-7.35 (m, 2H), 7.02-6.94 (m, 3H), 4.37 (q, J=7.1 Hz, 2H), 1.39 (t, J=7.1 Hz, 3H), 1.33 (s, 9H).

4-(4-(tert-Butyl)phenoxy)-3-fluorobenzoic acid (V142)

General procedure B: Ethyl 4-(4-(tert-butyl)phenoxy)-3-fluorobenzoate (V138) (341 mg, 1.08 mmol, 1.00 equiv) in a mixture of EtOH (3 mL) and 0.5 M NaOH (2 mL) was stirred at 80° C. for 1.5 h. Purification of the acidified crude product by column chromatography (DCM/MeOH 5%) gave the desired product as colourless solid (207 mg, 0.72 mmol, 67%); HRMS (ESI) m/z calcd. for $C_{17}H_{16}O_3F^-$ [M−H]$^-$ 287.1089, found: 287.1084; $^1$H NMR (400 MHz, Chloroform-d) δ 7.91 (dd, J=11.0, 2.0 Hz, 1H), 7.86-7.79 (m, 1H), 7.47-7.37 (m, 2H), 7.05-6.99 (m, 2H), 6.96 (t, J=8.3 Hz, 1H), 1.34 (s, 9H).

Ethyl 4-(4-(tert-pentyl)phenoxy)benzoate (V149)

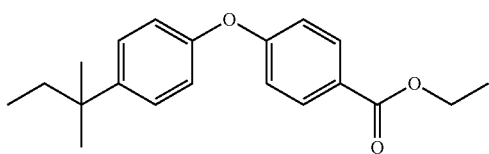

V149

General procedure A: Ethyl 4-fluorobenzoate (308 mg, 1.83 mmol, 1.00 equiv), 4-(tert-pentyl) phenol (380 mg, 2.32 mmol, 1.26 equiv) and $K_2CO_3$ (383 mg, 2.77 mmol, 1.51 equiv) in DMSO (4 mL) were stirred at 80° C. for 1 day and then at 120° C. for 2 days. Purification by column chromatography (EtOAc/petroleum ether 1:20) gave the desired product as colourless oil (476 mg, 1.52 mmol, 83%); HRMS (ESI) m/z calcd. for $C_{20}H_{25}O_3^+$ [M+H]$^+$ 313.1798, found: 313.1808; $^1$H NMR (400 MHz, Chloroform-d) δ 8.06-7.98 (m, 2H), 7.37-7.30 (m, 2H), 7.02-6.99 (m, 2H), 6.99-6.96 (m, 2H), 4.36 (q, J=7.1 Hz, 2H), 1.65 (q, J=7.4 Hz, 2H), 1.38 (t, J=7.1 Hz, 3H), 1.30 (s, 9H), 0.71 (t, J=7.4 Hz, 3H).

Ethyl 4-(4-((3r,5r,7r)-adamantan-1-yl)phenoxy)benzoate (V150)

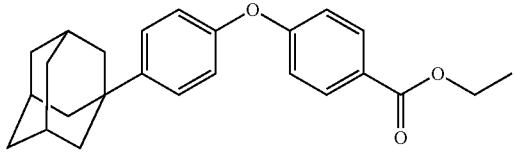

V150

General procedure A: Ethyl 4-fluorobenzoate (311 mg, 1.85 mmol, 1.00 equiv), 4-((3r,5r,7r)-adamantan-1-yl) phenol (522 mg, 2.29 mmol, 1.24 equiv) and $K_2CO_3$ (394 mg, 2.85 mmol, 1.54 equiv) in DMSO (4 mL) were stirred at 80° C. for 1 day and then at 120° C. for 2 days. Purification by column chromatography (EtOAc/petroleum ether 1:20) gave the desired product as colourless solid (551 mg, 1.46 mmol, 79%); HRMS (ESI) m/z calcd. for $C_{25}H_{29}O_3^+$ [M+H]$^+$ 377.2111, found: 377.2122; $^1$H NMR (400 MHz, Chloroform-d) δ 8.06-7.98 (m, 2H), 7.40-7.33 (m, 2H), 7.03-6.99 (m, 2H), 7.00-6.96 (m, 2H), 4.37 (q, J=7.1 Hz, 2H), 2.12 (m, 3H), 1.93 (m, 6H), 1.83-1.75 (m, 6H), 1.39 (t, J=7.1 Hz, 3H).

4-(4-(tert-Pentyl)phenoxy)benzoic acid (V151)

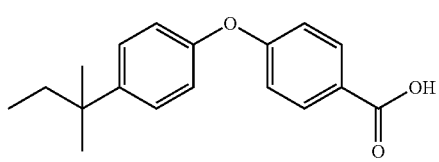

V151

General procedure B: Ethyl 4-(4-(tert-pentyl)phenoxy) benzoate (V149) (265 mg, 0.85 mmol, 1.00 equiv) in a mixture of EtOH (2.5 mL) and 0.5 M NaOH (2.5 mL) was stirred at 80° C. for 9 h. Purification of the acidified crude product by recrystallization from EtOAc gave the desired product as colourless solid (210 mg, 0.74 mmol, 87%); HRMS (ESI) m/z calcd. for $C_{18}H_{19}O_3^-$ [M−H]$^-$ 283.1340, found: 283.1343; $^1$H NMR (400 MHz, Chloroform-d) δ 8.12-8.01 (m, 2H), 7.39-7.31 (m, 2H), 7.03-7.01 (m, 2H), 7.01-6.98 (m, 2H), 1.66 (q, J=7.4 Hz, 2H), 1.31 (s, 9H), 0.71 (t, J=7.4 Hz, 3H).

4-(4-((3r,5r,7r)-Adamantan-1-yl)phenoxy)benzoic acid (V152)

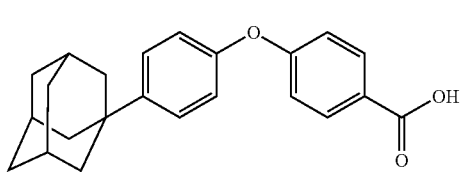

V152

General procedure B: Ethyl 4-(4-((3r,5r,70-adamantan-1-yl)phenoxy)benzoate (V150) (314 mg, 0.83 mmol, 1.00 equiv) in a mixture of EtOH (2.5 mL) and 0.5 M NaOH (2.5 mL) was stirred at 80° C. for 1 day. Purification of the acidified crude product by recrystallization from EtOAc gave the desired product as colourless solid (227 mg, 0.65 mmol, 78%); HRMS (ESI) m/z calcd. for $C_{23}H_{23}O_3^-$ [M−H]$^-$ 347.1653, found: 347.1648; $^1$H NMR (400 MHz, Chloroform-d) δ 8.06-8.03 (m, 2H), 7.40-7.36 (m, 2H), 7.04-7.01 (m, 2H), 7.01-6.98 (m, 2H), 2.11 (m, 3H), 1.93 (m, 6H), 1.78 (m, 6H).

Ethyl 4-(4-cyclohexylphenoxy)benzoate (V168)

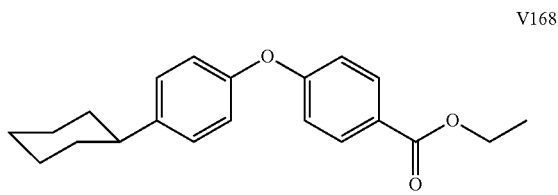 [SMILES: CCOC(=O)c1ccc(Oc2ccc(C3CCCCC3)cc2)cc1]

V168

General procedure A: Ethyl 4-fluorobenzoate (316 mg, 1.88 mmol, 1.00 equiv), 4-cyclohexylphenol (412 mg, 2.34 mmol, 1.24 equiv) and $K_2CO_3$ (418 mg, 3.03 mmol, 1.61 eq.) in DMSO (4 mL) were stirred at 120° C. for 2 days. Purification by column chromatography (EtOAc/petroleum ether 1/20) gave the desired product as colourless oil (483 mg, 1.49 mmol, 79%); HRMS (ESI) m/z calcd. for $C_{21}H_{25}O_3^+$ [M+H]$^+$ 325.1798, found: 325.1801; $^1$H NMR (400 MHz, Chloroform-d) δ 8.07-7.96 (m, 2H), 7.23-7.20 (m, 2H), 7.00-6.96 (m, 4H), 4.36 (q, J=7.1 Hz, 2H), 2.54-2.49 (m, 1H), 1.96-1.80 (m, 4H), 1.80-1.72 (m, 1H), 1.47-1.37 (m, 4H), 1.38 (t, J=7.1 Hz, 3H), 1.31-1.21 (m, 1H).

4-(4-Cyclohexylphenoxy)benzoic acid (V169)

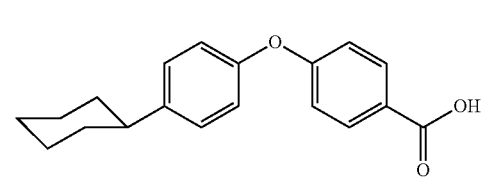

V169

General procedure B: Ethyl 4-(4-cyclohexylphenoxy) benzoate (V168) (236 mg, 0.73 mmol, 1.00 equiv) in a mixture of EtOH (3 mL) and 0.5 M NaOH (3 mL) was stirred at 80° C. for 5 h. Purification of the acidified crude product by recrystallization from EtOAc gave the desired product as colourless solid (158 mg, 0.53 mmol, 73%);

HRMS (ESI) m/z calcd. for $C_{19}H_{19}O_3$ [M−H]⁻ 295.1340, found: 295.1339; ¹H NMR (400 MHz, Chloroform-d) δ 8.06 (d, J=8.8 Hz, 1H), 7.23 (d, J=8.5 Hz, 2H), 7.24-6.98 (m, 4H), 2.55-2.49 (m, 1H), 1.91-1.85 (m, 4H), 1.78-1.75 (m, 1H), 1.47-1.35 (m, 4H), 1.31-1.21 (m, 1H).

BRIEF DESCRIPTION OF THE DRAWINGS

FIG. 3 Shows treatment of SCC13 cells with V126 resulted in increased protein expression of the differentiation marker involucrin. Cells were treated with DMSO or V126 at a concentration of 10 µM for 48 h. Total cell lysates were applied on Western Blot analysis using β-actin as loading control.

Biological Activity

Figure 1:
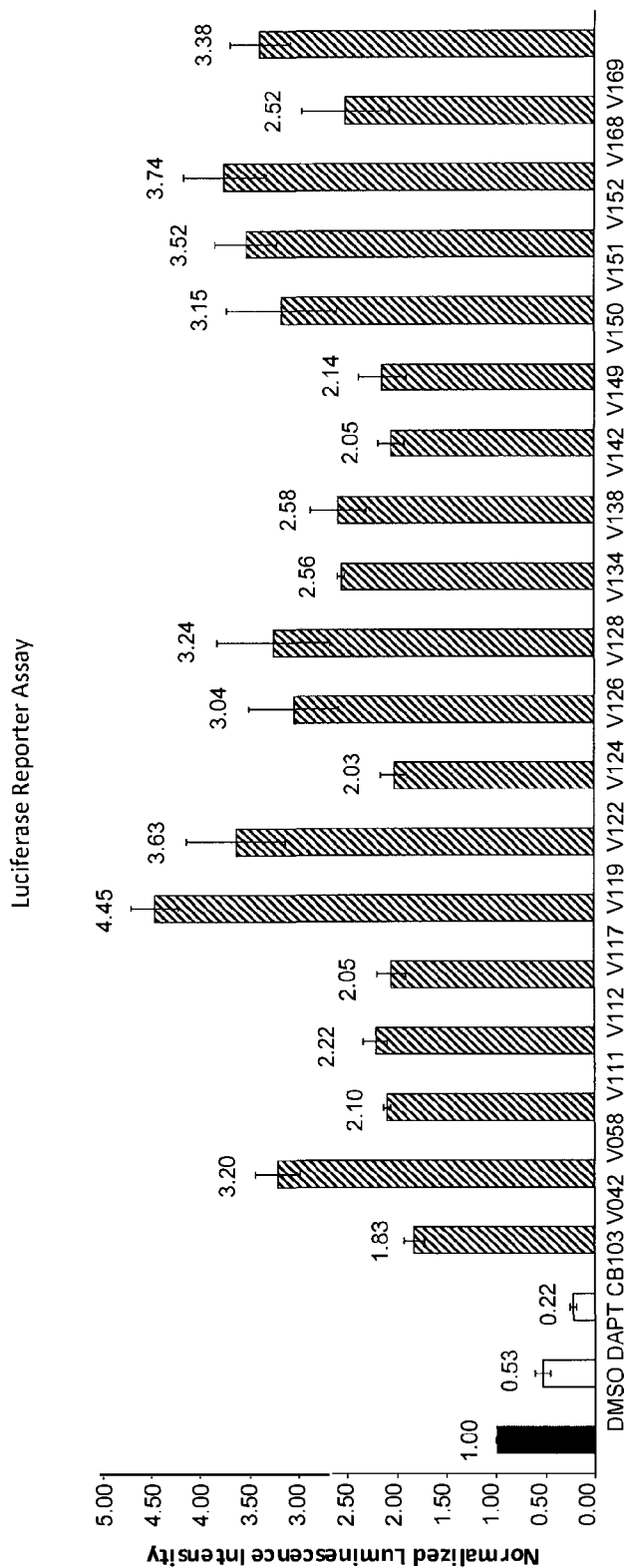
FIG. 1. Shows the enhancement of Notch signaling by the stated molecules in the luciferase reporter assay. The indicated compounds were tested at 10 µM concentration in a Notch-driven luciferase reporter assay. HeLa cells had been engineered to express the Notch1 full-length receptor, the firefly luciferase (expression dependent on Notch signaling) and the renilla luciferase (expression independent on Notch signaling). Cells were co-cultured in a 96 well-plate with DLL4 ligand expressing HeLa cells to induce Notch signaling and simultaneously treated with DMSO or indicated compounds for 20 h. Notch signaling activation was then quantified by measuring luciferase-dependent luminescence intensities upon treatment with appropriate substrates. The firefly values were normalized against the renilla values to obtain the relative luminescence intensities (represented by the bars). Control treatments with the y-secretase inhibitor DAPT or the Notch inhibitor CB103 (white) resulted in a decrease in Notch signaling relative to the DMSO control (black), whereas treatment with the indicated molecules led to an up to 4.5-fold increase in Notch signaling (diagonal lines).

The respective Notch signaling-enhancing activities of the preferred molecules depicted above in a Notch1-driven luciferase assay are illustrated in FIG. 1. A brief description of this Notch reporter assay is given in the caption of FIG. 1. Derivative V126 was tested as representative compound in further experiments.

Figure 2A:
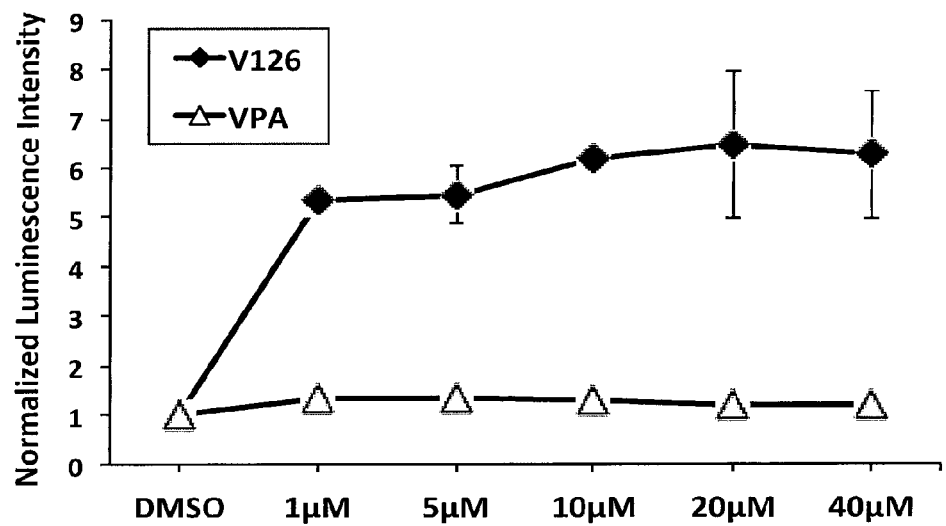
FIGS. 2A-2E Show that testing of derivative V126 in different settings within the luciferase reporter assay validated its Notch-enhancing property in vitro. A brief description of the assay is given in the description of FIG. 1. If not stated differently, all assays were performed using a Notch1 full-length receptor driven reporter system. Values are normalized against DMSO. a) V126 (black rhombi) was tested at the indicated concentrations. Valproic acid (VPA, white triangles) was included into the assay as positive control, but did not show any effect at concentrations up to 40 µM. b) Direct influence of V126 on the luciferase enzyme activity was examined by treatment with V126 at 10 µM and 1 µM 5 min prior to the readout (dotted, labeled "_test"). The control readouts for DMSO (black), CB103 (white), V126 at 10 µM and V126 at 1 µM (diagonal lines) were taken as usual after incubation for 20 h. c) V126 was tested in combination with an equimolar amount of the y-secretase inhibitor DAPT or the Notch inhibitor CB103 at 10 µM concentration each. d) V126 and the indicated compounds were tested at 10 µM in a luciferase reporter assay driven by the Notch2 receptor isoform. e) V126 and the indicated compounds were tested at 10 µM in a luciferase assay driven by the constitutively active form of the Notch1 receptor (N1ICD, Notch1 intracellular domain).
Figure 2B:
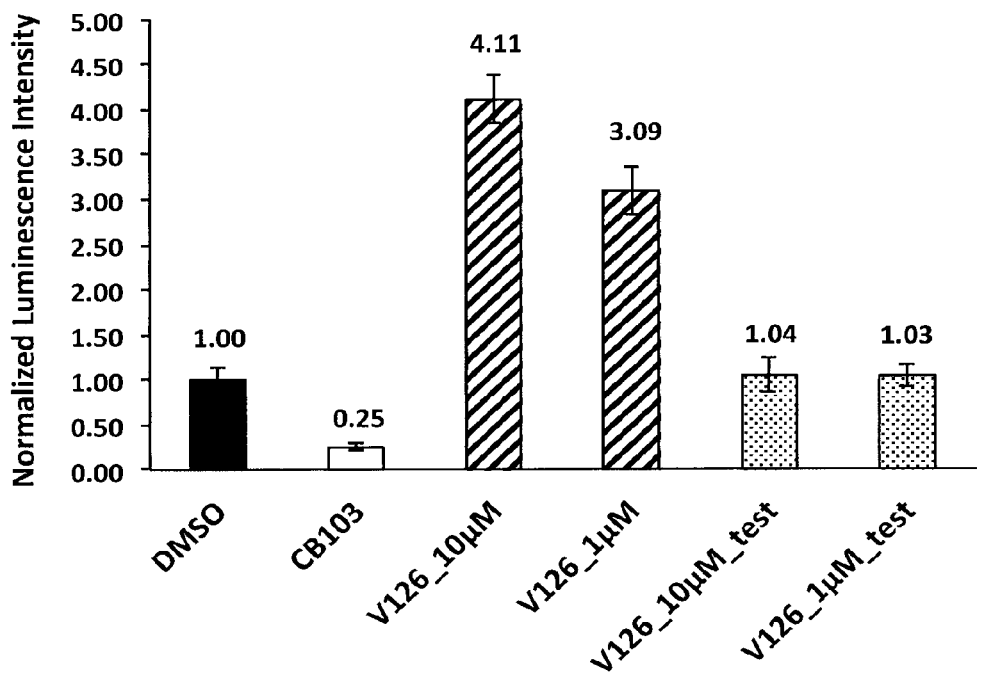
Figure 2:
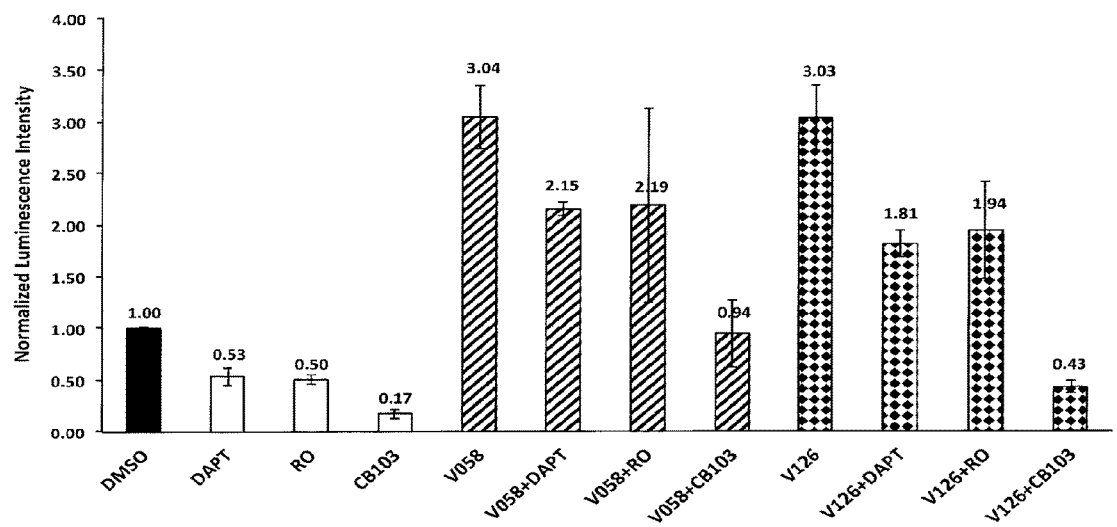
Figure 2:
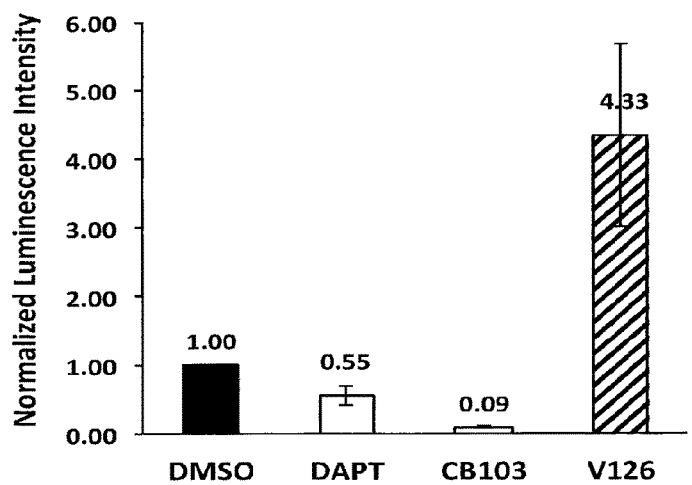

FIG. 2 shows investigations using V126 in different settings within the luciferase reporter assay. V126 strongly enhanced Notch signaling already at a concentration of 1↔M, whereas the reported Notch enhancer valproic acid did not show any effect within the frame of the screened concentrations of up to 40-M (FIG. 2a). To rule out that V126 is directly enhancing the activity of the luciferase enzyme, the Notch reporter assay was challenged by applying V126 treatment immediately prior to the readout. Short-term treatment yielded values in the range of the DMSO control level, whereas the corresponding treatment with V126 for 20 h in the very same readout resulted in the expected upregulation of the luciferase values (FIG. 2b). This strongly suggests that the increased luciferase values are truly derived from enhanced reporter gene expression. Moreover, the Notch-enhancing activity of V126 could be partially and completely rescued by combinational equimolar treatment with the γ-secretase inhibitor DAPT or the Notch inhibitor CB103, respectively, further confirming the ability of V126 to upregulate Notch signaling (FIG. 2c). Testing of V126 in luciferase assays that are driven by the Notch2 receptor isoform (N2FL, Notch2 full-length receptor) or by the truncated, constitutively active form of the Notch1 receptor (N1ICD, Notch1 intracellular domain) indicated that V126 is able not only to enhance signaling derived from different Notch receptor isoforms, but also to enhance the signaling cascade taking place downstream of ligand-mediated activation of Notch signaling (FIGS. 2d and e).

Figure 4:
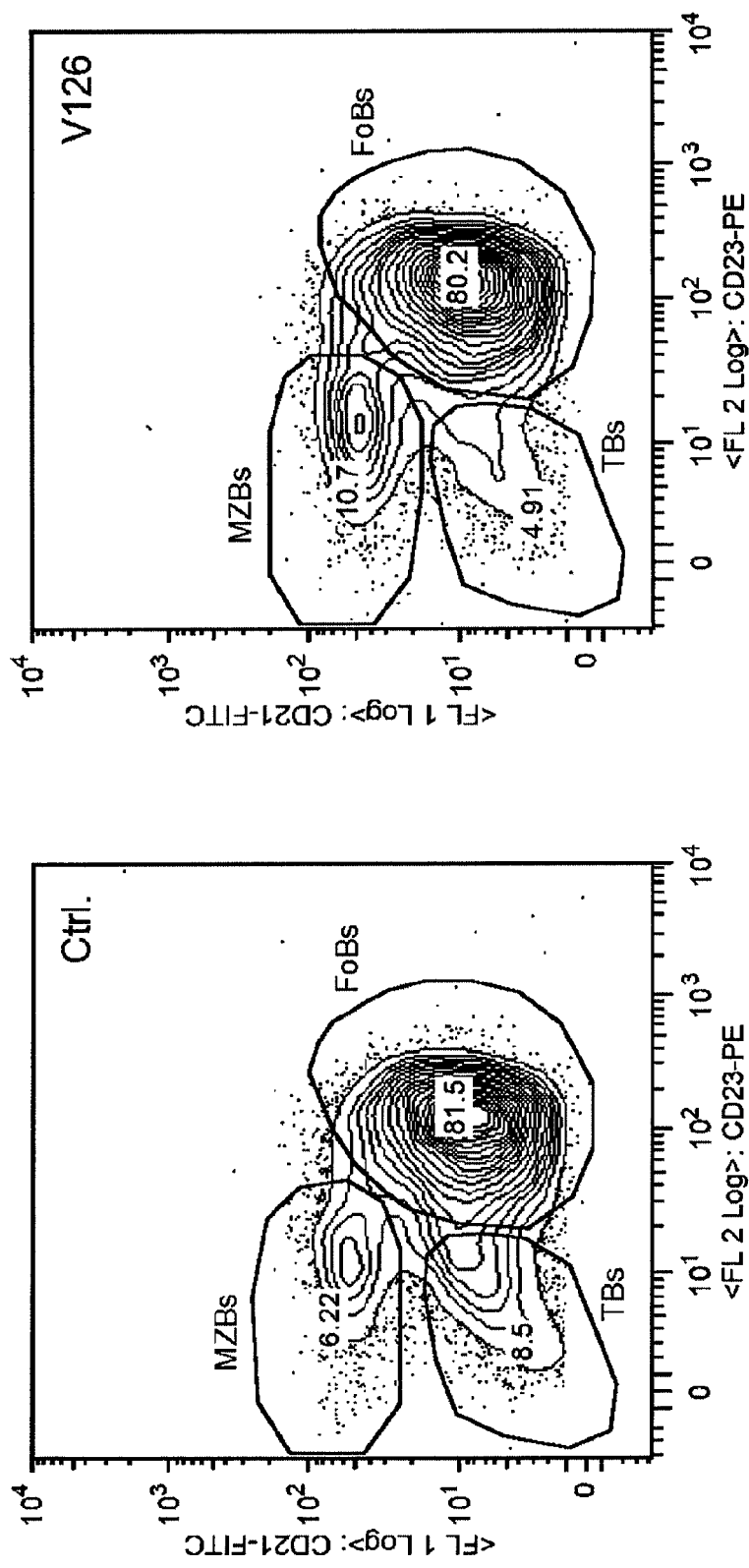
FIGS. 4A-4B Shows in vivo application of V126 led to an increase of splenic marginal zone B-cell (MZB) numbers. C57BL/6N mice were treated with 25 mg/kg V126 by intraperitoneal injection once a day for one week. a) Spleen cells were analyzed by flow cytometry. Shown are two representative plots of control (Ctrl., n=5) and V126 (n=4) treatments displaying the B220+cell (total B-cell) population. The gates encircle the respective MZB, FoB, and TB fractions with the corresponding numbers indicating the relative proportions (in percentage) of cells out of the B220+population. b) The bar diagrams quantify the relative MZB percentages from a) (left), and the recalculated total numbers of splenic MZBs (right). FoBs: Follicular B-cells, TBs: Transitional B-cells, see text.
Figure 4:
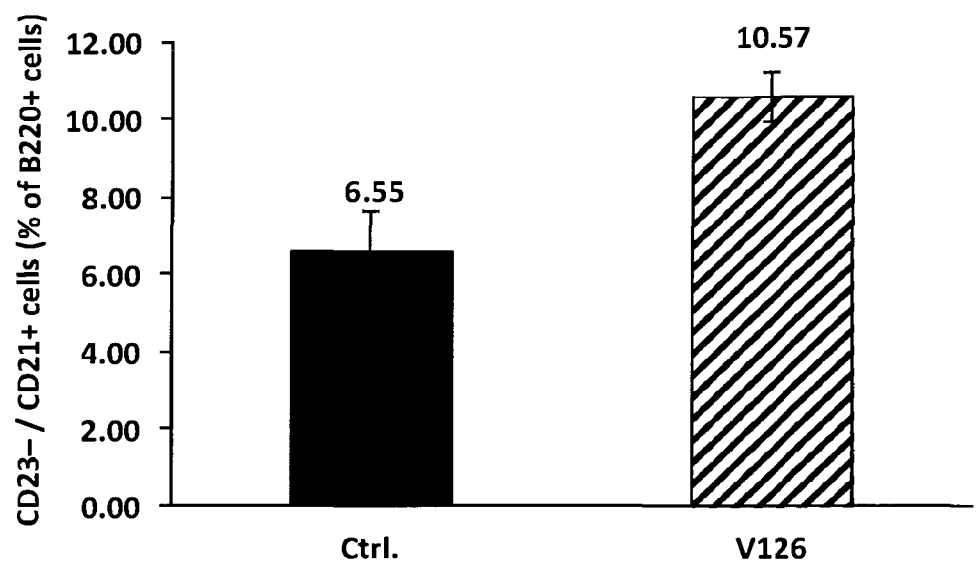
Figure 4:
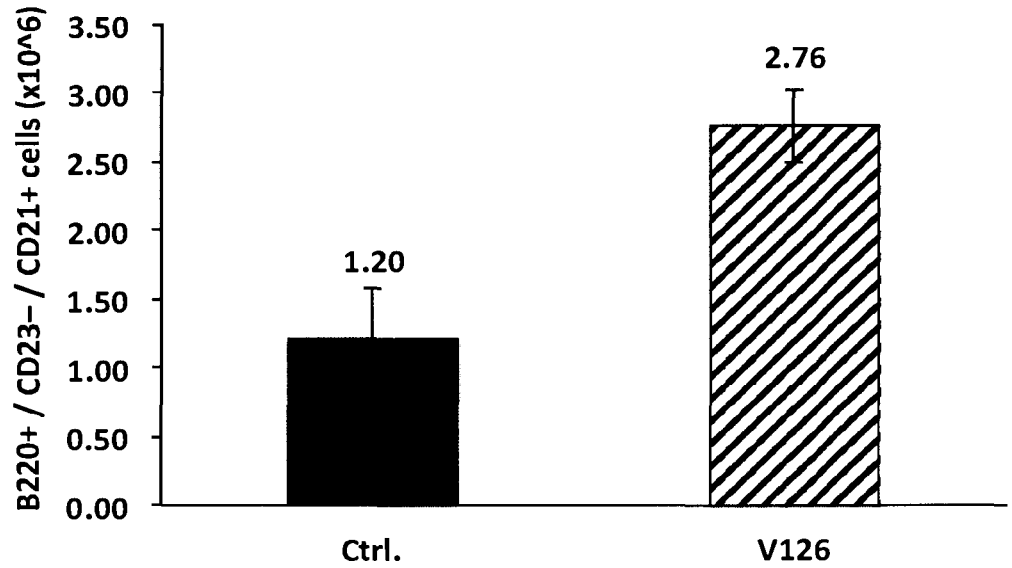
Figure 5:
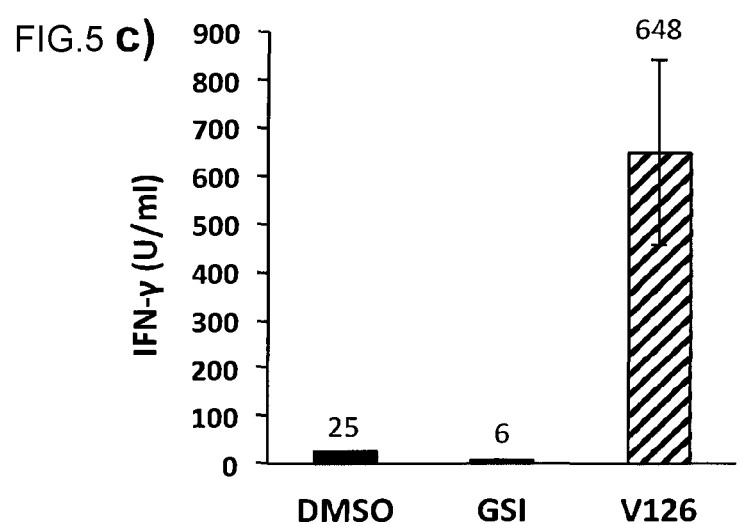
FIGS. 5A-5C The Notch signaling enhancing compound V126 induces increased IFNy production and secretion in vitro. CD4 T cells isolated from naive CS7B/6 mice were cultured on plate bound α-CD3/α-CD28 (both 0.25µg/ml) under Th1 polarizing conditions (rIL-12, (5ng/ml) and anti-IL-4 (clone:11B11; 20mg/ml)) in the presence of DMSO, DAPT as y-secretase inhibitor and V126 at 10 µM. 96 hours after initiation of the culture, intracellular IFN-y levels a) and CD25 surface expression b) were assessed on PMA/Ionomycin stimulated CD4 T cells. c) IFN-y cytokine levels were assessed in culture supernatants by Elisa under the same conditions as in a) and b).

Notch activation in the skin is known to drive differentiation of keratinocytes resulting in the induction of differentiation markers such as involucrin (C. Nowell, Cold Spring Harb Perspect Med. 2013, 3, 12), (G. P. Dotto, Oncogene 2008, 27, 5115-5123). Therefore, V126 was further investigated by treatment of the human squamous cell carcinoma cell line SCC13 at a concentration of 10↔M. Increased expression of involucrin at the protein level was detected upon incubation with V126 for 48 h (FIG. 3), suggesting that V126 is promoting differentiation in this cancer cell line via upregulation of Notch signaling. In the spleen, marginal zone B-cells (MZBs) and follicular B-cells (FoBs) are the two main types of mature B-cells, both of which develop from the same precursor cells, namely the transitional B-cells (TBs). Notch2 signaling was reported to play a crucial role in the development of MZBs (S. Pillai, Nat. Rev. Immunol. 2009, 9, 767-777) and increased Notch2 signaling in the spleen leads to an expansion of the MZB compartment (F. Hampel, Blood 2011, 118, 24, 6321-6331). In contrast, the development of FoBs is not dependent on Notch signaling. To evaluate the effect of V126 in vivo, C57BL/6N mice were injected intraperitoneally with 25 mg/kg V126 once a day for one week. The impact of V126 on the different B-cell compartments in these mice was analyzed by flow cytometry on splenocytes, showing that V126 was capable to double the number of MZBs as compared to the control, whereas the FoB numbers were not affected (FIG. 4).

In conclusion, these results indicate that V126 is enhancing Notch signaling in vitro and in vivo.

The invention claimed is:

1. A method for treating a patient suffering from a Notch associated disease selected from the group consisting of: atopic dermatitis, psoriasis, immune related disorders, squamous cell carcinoma, cutaneous and lung squamous cell carcinoma, head and neck cancer, non-melanoma skin cancer, basal cell carcinoma and actinic keratosis, neuroendocrine tumors, neuroendocrine small cell carcinoma and carcinoid tumors, thyroid carcinomas, muscular disorders, muscular dystrophy, impaired regeneration capacity after muscle injury; or for treating a patient undergoing immunotherapy for cancer, comprising administering a pharmaceutical compound of the general formula (I).

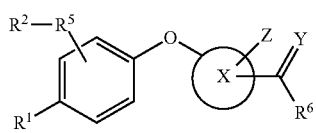

(I)

wherein
X is an aromatic cycle selected from a phenylene ring $C_6H_4$, in which one or more H atoms are optionally replaced independently by one or more of the substituents Z; or X is a 6-membered aromatic heterocycle selected from the group consisting of pyridine, pyridazine, pyrimidine and pyrazine, in which one or more H atoms are optionally replaced independently by one or more of the substituents Z;

R1 is selected from: H; linear and branched, unsubstituted and substituted $C_1$-$C_{16}$ alkyl; linear and branched, unsubstituted and substituted $C_2$-$C_8$ alkenyl; linear and branched, unsubstituted and substituted $C_2$-$C_8$ alkynyl; substituted and unsubstituted $C_3$-$C_8$ cycloalkyl; substituted and unsubstituted $C_5$-$C_8$ cycloalkenyl; adamantyl and norbornyl; and wherein the substituents of the named alkyl, alkenyl, alkynyl, cycloalkyl, cycloalkenyl, adamantyl and norbornyl groups are selected from the group F, Cl, Br, I, -CN, -NCO, -NCS, $N_3$, and wherein the named groups can be single or multiple substituted;

$R^2$-$R^5$ are independently of each other selected from: H, F, Cl, Br, I; linear and branched, unsubstituted and substituted $C_1$-$C_4$ alkyl, $C_2$-$C_4$ alkenyl and $C_2$-$C_4$ alkynyl, cyclopropyl and cyclobutyl, and wherein the substituents of the named alkyl, alkenyl, alkynyl, cyclopropyl and cyclobutyl groups are selected from F, Cl, Br and I;

Y is O or S;

Z is selected from the group consisting of F, Cl, Br, linear and branched, unsubstituted and substituted $C_1$-$C_4$ alkyl, $C_2$-$C_4$ alkenyl, $C_2$-$C_4$ alkynyl, cyclopropyl and cyclobutyl, and wherein the substituents of the named alkyl, alkenyl, alkynyl, cyclopropyl and cyclobutyl groups are selected from the group consisting of F, Cl, Br and I;

$R^6$ is selected from: $OR^7$, $NR^8 R^9$, NHOH;
$R^7$ is selected from H and linear and branched $C_1$-$C_6$ alkyl;
$R^8$ and $R^9$ are independently of each other selected from H and linear and branched $C_1$-$C_6$ alkyl; and/or a pharmaceutically acceptable salt or ester thereof, wherein when X is a phenylene ring in said pharmaceutical compound, the phenylene ring X is not substituted by Cl (substituent Z).

2. The method according to claim 1, wherein when X is a phenylene ring in said pharmaceutical compound, $R^1$ is selected from linear and branched, unsubstituted and substituted $C_4$-$C_{16}$ alkyl; linear and branched, substituted and unsubstituted $C_4$-$C_8$ alkenyl; linear and branched, unsubstituted and substituted $C_4$-$C_8$ alkynyl; substituted and unsubstituted $C_4$-$C_8$ cycloalkyl; substituted and unsubstituted $C_5$-$C_8$ cycloalkenyl; adamantyl and norbornyl; and wherein the substituents of the named alkyl, alkenyl, alkynyl, cycloalkyl, cycloalkenyl, adamantyl and norbornyl groups are selected from the group consisting of F, Cl, Br, I, —CN, —NCO, —NCS, and $N_3$, and wherein the named groups can be single or multiple substituted.

3. The method according to claim 1, wherein when X is a phenylene ring in said pharmaceutical compound, the phenylene ring X is not substituted by F, Cl, or Br (substituent Z) in position 2 and 6 with respect to the ether group, and at least one of $R^2$-$R^5$ and Z is a substituent other than H, when $R^1$ is H or $CH_3$.

4. The method according to claim 1,
wherein when X is a heterocycle selected from pyridine, pyridazine, pyrimidine and pyrazine in said compound:
$R^1$ is selected from: H; linear and branched, unsubstituted and substituted $C_1$-$C_{12}$ alkyl; linear and branched, unsubstituted and substituted $C_2$-$C_8$ alkenyl; linear and branched, unsubstituted and substituted $C_2$-$C_8$ alkynyl; substituted and unsubstituted $C_3$-$C_8$ cycloalkyl; substituted and unsubstituted $C_6$-$C_8$ cycloalkenyl; adamantyl and norbornyl; and wherein the substituents of the named alkyl, alkenyl, alkynyl, cycloalkyl, cycloalkenyl, adamantyl and norbornyl groups are selected from the group F, Cl, Br, I, —CN, —NCO, —NCS, $N_3$, and wherein the named groups can be single or multiple substituted;
$R^2$-$R^5$ are independently of each other selected from: H, F, Cl, Br, I; unsubstituted and substituted $C_1$-$C_2$ alkyl, $C_2$-alkenyl, $C_2$-alkynyl, and wherein the substituent of the named alkyl, alkenyl, and alkynyl groups is F;
Z is selected from F, Cl, Br, I; unsubstituted and substituted $C_1$-$C_2$ alkyl, $C_2$-alkenyl, $C_{-2}$ alkynyl, and wherein the substituent of the named alkyl, alkenyl and alkynyl is F;
R7 is selected from H and linear and branched $C_1$-$C_4$ alkyl;
$R^8$ and $R^9$ are independently of each other selected from H and linear and branched $C_1$-$C_4$ alkyl;
and/or a pharmaceutically acceptable salt or ester thereof.

5. The method according to claim 1, wherein in said pharmaceutical compound,
$R^1$ is selected from: H; linear and branched, unsubstituted and substituted $C_1$-$C_8$ alkyl; linear and branched, unsubstituted and substituted $C_2$-$C_6$ alkenyl; linear and branched, unsubstituted and substituted $C_2$-$C_6$ alkynyl; substituted and unsubstituted $C_3$-$C_6$ cycloalkyl; substituted and unsubstituted $C_5$-$C_6$ cycloalkenyl; adamantyl and norbornyl; and wherein the substituents of the named alkyl, alkenyl, alkynyl, cycloalkyl, cycloalkenyl, adamantyl and norbornyl groups are selected from the group consisting of F, Cl, Br, I, —CN, —NCO, —NCS, and $N_3$, and wherein the named groups can be single or multiple substituted;

$R^2$-$R^5$ are independently of each other selected from the group consisting of: H, F, Cl, Br, I; unsubstituted and substituted $C_1$-$C_2$ alkyl, $C_2$-alkenyl, and $C_2$-alkynyl, and wherein the substituents of the named alkyl, alkenyl and alkynyl groups are F;

and/or a pharmaceutically acceptable salt or ester thereof.

6. The method according to claim 1, wherein in said pharmaceutical compound

X is pyridine, in which one or more H atoms are optionally replaced independently by one or more of the substituents Z;

$R^1$ is selected from: H; linear and branched, unsubstituted and substituted $C_1$-$C_6$ alkyl; linear and branched, unsubstituted and substituted $C_2$-$C_6$ alkenyl; linear and branched, unsubstituted and substituted $C_2$-$C_6$ alkynyl; substituted and unsubstituted $C_3$-$C_6$ cycloalkyl; substituted and unsubstituted $C_5$-$C_6$ cycloalkenyl; adamantyl and norbornyl; and wherein the substituents of the named alkyl, alkenyl, alkynyl, cycloalkyl, cycloalkenyl, adamantyl and norbornyl groups are F, and wherein the named groups can be single or multiple substituted; and/or a pharmaceutically acceptable salt or ester thereof.

7. The method according to claim 1, wherein $R^1$ is selected from: H; linear and branched, unsubstituted and substituted $C_1$-$C_6$ alkyl; substituted and unsubstituted $C_3$-$C_6$ cycloalkyl; adamantyl and norbornyl; and wherein the substituents of the named alkyl, cycloalkyl, adamantyl and norbornyl groups are F, and wherein the named groups can be single or multiple substituted;

$R^2$-$R^5$ are independently of each other selected from: H; F; unsubstituted and substituted $C_1$-$C_2$ alkyl, and wherein the substituents of the named alkyl groups are F;

Y is O,

Z is selected from the group consisting of F, Cl, Br, and unsubstituted and substituted $C_1$-$C_2$ alkyl, and wherein the substituents of the named alkyl groups are F;

$R^6$ is selected from the group consisting of: $OR^7$, and $NR^8R^9$;

and/or a pharmaceutically acceptable salt or ester thereof.

8. The method according to claim 1, wherein the individual is a mammal, preferably a human.

9. The method according to claim 1, wherein said disease is associated with reduced Notch signaling activity.

10. The method as defined in claim 1, wherein in said pharmaceutical compound, $R^6$ is selected from $OR^7$, $NR^8R^9$ and NHOH, and $R^7$ is selected from linear and branched $C_1$-$C_6$ alkyl.

11. The method as defined in claim 1, wherein when X is a phenylene ring, $R^1$ is selected from linear and branched, unsubstituted and substituted $C_4$-$C_{16}$ alkyl; linear and branched, substituted and unsubstituted $C_4$-$C_8$ alkenyl; linear and branched, substituted and unsubstituted $C_4$-$C_8$ alkynyl; substituted and unsubstituted $C_4$ cycloalkyl, $C_5$ cycloalkyl, $C_7$ cycloalkyl, $C_8$ cycloalkyl; substituted and unsubstituted $C_5$-$C_8$ cycloalkenyl; adamantyl and norbornyl; and wherein the substituents of the named alkyl, alkenyl, alkynyl, cycloalkyl, cycloalkenyl, adamantyl and norbornyl groups are selected from the group consisting of F, Cl, Br, I, —CN, —NCO, —NCS, $N_3$, and wherein the named groups can be single or multiple substituted, or wherein when X is a heterocycle selected from pyridine, pyridazine, pyrimidine and pyrazine:

$R^1$ is selected from: linear and branched, unsubstituted and substituted $C_2$ alkyl, $C_3$ alkyl, $C_4$ alkyl, $C_5$ alkyl, $C_6$ alkyl, $C_7$ alkyl, $C_8$ alkyl, $C_9$ alkyl, $C_{10}$ alkyl, $C_{11}$ alkyl, $C_{12}$ alkyl; linear and branched, unsubstituted and substituted $C_2$-$C_8$ alkenyl; linear and branched, unsubstituted and substituted $C_2$-$C_8$ alkynyl; substituted and unsubstituted $C_3$-$C_8$ cycloalkyl; substituted and unsubstituted $C_5$-$C_8$ cycloalkenyl; adamantyl and norbornyl; and wherein the substituents of the named alkyl, alkenyl, alkynyl, cycloalkyl, cycloalkenyl, adamantyl and norbornyl groups are selected from the group consisting of F, Cl, Br, I, —CN, —NCO, —NCS, $N_3$, and wherein the named groups can be single or multiple substituted;

$R^2$-$R^5$ are independently of each other selected from the group consisting of: H, F, Cl, Br, I; unsubstituted and substituted $C_1$-$C_2$ alkyl, $C_2$-alkenyl, $C_2$-alkynyl, and wherein the substituent of the named alkyl, alkenyl, and alkynyl groups is F;

Z is selected from F, Cl, Br; unsubstituted and substituted $C_1$-$C_2$ alkyl, $C_2$-alkenyl, $C_2$-alkynyl, and wherein the substituent of the named alkyl, alkenyl and alkynyl groups is F;

$R^7$ is selected from H and linear and branched $C_1$-$C_4$ alkyl;

$R^8$ and $R^9$ are independently of each other selected from H and linear and branched $C_1$-$C_4$ alkyl;

and/or a pharmaceutically acceptable salt or ester thereof.

12. The method according to claim 11, wherein said patient is a mammal, preferably a human.

13. The method according to claim 1, wherein prior to administration, the pharmaceutical compound is prepared by a method comprising the steps of coupling, preferably via $S_NAr$ coupling, of a substituted phenol with an electron-poor aromatic or heteroaromatic halide, and derivatizing the obtained biaryl ethers by hydrolysis, esterification or amidation.

14. The method according to claim 1, wherein in said pharmaceutical compound $R^1$ is selected from: linear and branched, unsubstituted and substituted $C_6$ alkyl, $C_7$ alkyl, $C_8$ alkyl, $C_9$ alkyl, $C_{10}$ alkyl, $C_{11}$ alkyl, $C_{12}$ alkyl, $C_{13}$ alkyl, $C_{14}$ alkyl, $C_{15}$ alkyl, $C_{16}$ alkyl; linear and branched, unsubstituted and substituted $C_4$-$C_8$ alkenyl; linear and branched, unsubstituted and substituted $C_4$-$C_8$ alkynyl; substituted and unsubstituted $C_4$-$C_8$ cycloalkyl; substituted and unsubstituted $C_5$-$C_8$ cycloalkenyl; adamantyl and norbornyl; and wherein the substituents of the named alkyl, alkenyl, alkynyl, cycloalkyl, cycloalkenyl, adamantyl and norbornyl groups are selected from the group consisting of F, Cl, Br, I, —CN, —NCO, —NCS, and $N_3$, and wherein the named groups can be single or multiple substituted; wherein $R^6$ is selected from the group consisting of $OR^7$, $NR^8R^9$ and NHOH, and $R^7$ is selected from linear and branched $C_2$ alkyl, $C_3$ alkyl, $C_4$ alkyl, $C_5$ alkyl, and $C_6$ alkyl.

15. The method according to claim 1, wherein in said pharmaceutical compound when X is a phenylene ring, $R^1$ is selected from the group consisting of branched, unsubstituted and substituted $C_6$ alkyl, $C_7$ alkyl, $C_8$ alkyl, $C_9$ alkyl, $C_{10}$ alkyl, $C_{11}$ alkyl, $C_{12}$ alkyl, $C_{13}$ alkyl, $C_{14}$ alkyl, $C_{15}$ alkyl, $C_{16}$ alkyl; linear and branched, substituted and unsubstituted $C_4$-$C_8$ alkenyl; linear and branched, unsubstituted and substituted $C_4$-$C_8$ alkynyl; substituted and unsubstituted $C_4$ cycloalkyl, $C_5$ cycloalkyl, $C_7$ cycloalkyl, $C_8$ cycloalkyl; substituted and unsubstituted $C_5$-$C_8$ cycloalkenyl; adamantyl and norbornyl; and wherein the substituents of the named alkyl, alkenyl, alkynyl, cycloalkyl, cycloalkenyl, adamantyl and norbornyl groups are selected from the group consisting of F, Cl, Br, I, —CN, —NCO, —NCS, and $N_3$, and wherein the named groups can be single or multiple substituted, or wherein when X is a heterocycle selected from pyridine, pyridazine, pyrimidine and pyrazine:

$R_1$ is selected from the group consisting of linear and branched, unsubstituted and substituted $C_6$ alkyl, $C_7$ alkyl, $C_8$ alkyl, $C_9$ alkyl, $C_{10}$ alkyl, $C_{11}$ alkyl, $C_{12}$ alkyl; linear and branched, unsubstituted and substituted $C_2$-$C_8$ alkenyl; linear and branched, unsubstituted and substituted $C_2$-$C_8$ alkynyl; substituted and unsubstituted $C_3$-$C_8$ cycloalkyl; substituted and unsubstituted $C_5$-$C_8$ cycloalkenyl; adamantyl and norbornyl; and wherein the substituents of the named alkyl, alkenyl, alkynyl, cycloalkyl, cycloalkenyl, adamantyl and norbornyl groups are selected from the group consisting of F, Cl, Br, I, —CN, —NCO, —NCS, and $N_3$, and wherein the named groups can be single or multiple substituted;

$R^2$-$R^5$ are independently of each other selected from the group consisting of H, F, Cl, Br, I; unsubstituted and substituted $C_1$-$C_2$ alkyl, $C_2$-alkenyl, $C_2$-alkynyl, and wherein the substituent of the named alkyl, alkenyl, and alkynyl groups is F;

Z is selected from the group consisting of F, Cl, Br; unsubstituted and substituted $C_1$-$C_2$ alkyl, $C_2$-alkenyl, $C_2$-alkynyl, and wherein the substituent of the named alkyl, alkenyl and alkynyl groups is F;

$R^7$ is selected from H and linear and branched $C_1$-$C_4$ alkyl;

$R^8$ and $R^9$ are independently of each other selected from H and linear and branched $C_1$-$C_4$ alkyl;

and/or a pharmaceutically acceptable salt or ester thereof.

16. The method according to claim 1, wherein in said pharmaceutical compound, $R^6$ is selected from the group consisting of $OR^7$, $NR^8R^9$ and NHOH, and $R^7$ is selected from linear and branched $C_1$-$C_6$ alkyl or a pharmaceutically acceptable salt or ester thereof, and said compound is in admixture with an inert carrier.

17. The method according to claim 1, wherein said mammal is a human.

* * * * *